(12) United States Patent
Webster et al.

(10) Patent No.: US 8,758,325 B2
(45) Date of Patent: Jun. 24, 2014

(54) RAPID EXCHANGE CATHETER

(75) Inventors: Mark W. I. Webster, Auckland (NZ); Jason A. Galdonik, Hanover, MN (US); Matthew F. Ogle, Fitchburg, WI (US); Edward Anderson, Maple Grove, MN (US); Gregory A. Boldenow, St. Michael, MN (US)

(73) Assignee: Medtronic, Inc., Minneapolis, MN (US)

( * ) Notice: Subject to any disclaimer, the term of this patent is extended or adjusted under 35 U.S.C. 154(b) by 2127 days.

(21) Appl. No.: 11/409,147

(22) Filed: Apr. 21, 2006

(65) Prior Publication Data

US 2007/0060911 A1    Mar. 15, 2007

Related U.S. Application Data

(63) Continuation of application No. 11/206,680, filed on Aug. 18, 2005.

(51) Int. Cl.
*A61M 31/00* (2006.01)

(52) U.S. Cl.
USPC .......................................................... 604/510

(58) Field of Classification Search
CPC ................ A61B 2017/1205; A61B 17/12113; A61B 2017/00778; A61M 2025/0183; A61M 25/0068; A61M 25/008
USPC ............. 604/22, 35, 523, 524, 525, 528, 529, 604/103.04, 509
See application file for complete search history.

(56) References Cited

U.S. PATENT DOCUMENTS

| | | | |
|---|---|---|---|
| 4,020,829 A | 5/1977 | Willson et al. | |
| 4,033,331 A | 7/1977 | Guss et al. | |
| 4,610,662 A | 9/1986 | Weikl et al. | |
| 4,676,249 A | 6/1987 | Arenas et al. | |
| 4,723,549 A | 2/1988 | Wholey et al. | |

(Continued)

FOREIGN PATENT DOCUMENTS

| | | |
|---|---|---|
| WO | WO 95/05209 | 2/1995 |
| WO | WO 98/38930 | 9/1998 |
| WO | WO 02/085092 | 10/2002 |

OTHER PUBLICATIONS

Feldman, "Transcatheter Aspiration of a Thrombus in an Aortocoronary Saphenous Vein Graft," *Am. J. Cardiol.* Aug. 1, 1987, 60(4), 379-380.

(Continued)

*Primary Examiner* — Aarti B Berdichevsky
*Assistant Examiner* — Bradley Osinski

(57) ABSTRACT

Thrombectomy catheters are presented that have curved tip portions. A suction lumen extends from at or near the proximal end of the catheter to a suction port at or near the tip portion of the catheter. The curves of the thrombectomy catheter can be selected to place a suction port at or near a vessel wall for the more effective removal of thrombus resulting from directing the suction in the direction of the thrombus. In some embodiments, the tip portion of the catheter can be transitioned from a first configuration for delivery of the catheter into the vessel to a second more curved configuration with a desired design for application of suction. The catheter can be moved in a circumferential and/or lateral direction to cover selected portions of the inner vessel wall. In some embodiments, a partially occlusive structure can be used to reduce and/or redirect flow within the vessel to improve performance of the thrombectomy.

18 Claims, 20 Drawing Sheets

(56) References Cited

U.S. PATENT DOCUMENTS

| | | | |
|---|---|---|---|
| 4,728,319 A | 3/1988 | Masch | |
| 4,784,636 A | 11/1988 | Rydell | |
| 4,790,812 A | 12/1988 | Hawkins, Jr. et al. | |
| 4,794,928 A | 1/1989 | Kletschka | |
| 4,873,978 A | 10/1989 | Ginsburg | |
| 4,883,460 A | 11/1989 | Zanetti | |
| 4,887,613 A | 12/1989 | Farr et al. | |
| 4,994,067 A | 2/1991 | Summers | |
| 5,011,488 A | 4/1991 | Ginsburg | |
| 5,011,490 A | 4/1991 | Fischell et al. | |
| 5,053,008 A | 10/1991 | Bajaj | |
| 5,059,178 A | 10/1991 | Ya | |
| 5,102,415 A | 4/1992 | Guenther et al. | |
| 5,108,419 A | 4/1992 | Reger et al. | |
| 5,152,277 A | 10/1992 | Honda et al. | |
| 5,163,906 A | 11/1992 | Ahmadi | |
| 5,211,651 A | 5/1993 | Reger et al. | |
| 5,308,318 A * | 5/1994 | Plassche, Jr. | 604/540 |
| 5,549,626 A | 8/1996 | Miller et al. | |
| 5,599,307 A | 2/1997 | Bacher et al. | |
| 5,766,191 A | 6/1998 | Trerotola | |
| 5,814,064 A | 9/1998 | Daniel et al. | |
| 5,827,229 A * | 10/1998 | Auth et al. | 604/171 |
| 5,836,868 A | 11/1998 | Ressemann et al. | |
| 5,843,051 A | 12/1998 | Adams et al. | |
| 5,897,567 A | 4/1999 | Ressemann et al. | |
| 5,911,725 A | 6/1999 | Boury | |
| 5,911,734 A | 6/1999 | Tsugita et al. | |
| 5,938,645 A * | 8/1999 | Gordon | 604/264 |
| 5,941,869 A | 8/1999 | Patterson et al. | |
| 5,997,557 A | 12/1999 | Barbut et al. | |
| 6,010,522 A | 1/2000 | Barbut et al. | |
| 6,022,336 A | 2/2000 | Zadno-Azizi et al. | |
| 6,135,991 A | 10/2000 | Muni et al. | |
| 6,142,987 A | 11/2000 | Tsugita | |
| 6,159,195 A | 12/2000 | Ha et al. | |
| 6,168,579 B1 | 1/2001 | Tsugita | |
| 6,203,561 B1 | 3/2001 | Ramee et al. | |
| 6,206,868 B1 | 3/2001 | Parodi | |
| 6,270,477 B1 | 8/2001 | Bagaoisan et al. | |
| 6,361,545 B1 | 3/2002 | Macoviak et al. | |
| 6,454,741 B1 | 9/2002 | Muni et al. | |
| 6,485,500 B1 | 11/2002 | Kokish | |
| 6,569,148 B2 | 5/2003 | Bagaoisan et al. | |
| 6,596,011 B2 | 7/2003 | Johnson et al. | |
| 6,620,148 B1 | 9/2003 | Tsugita | |
| 6,805,684 B2 | 10/2004 | Bonnette et al. | |
| 6,805,692 B2 | 10/2004 | Muni et al. | |
| 6,879,854 B2 * | 4/2005 | Windheuser et al. | 600/434 |
| 6,958,059 B2 | 10/2005 | Zadno-Azizi | |
| 7,115,134 B2 | 10/2006 | Chambers | |
| 7,166,120 B2 | 1/2007 | Kusleika | |
| 7,229,431 B2 * | 6/2007 | Houser et al. | 604/103.04 |
| 7,229,464 B2 | 6/2007 | Hanson et al. | |
| 2001/0051811 A1 | 12/2001 | Bonnette et al. | |
| 2002/0010411 A1 | 1/2002 | Macoviak et al. | |
| 2002/0035347 A1 | 3/2002 | Bagaoisan | |
| 2002/0165574 A1 | 11/2002 | Resseman et al. | |
| 2002/0169472 A1 | 11/2002 | Douk et al. | |
| 2003/0023263 A1 * | 1/2003 | Krolik et al. | 606/200 |
| 2003/0120208 A1 * | 6/2003 | Houser et al. | 604/103.04 |
| 2003/0135232 A1 | 7/2003 | Douk et al. | |
| 2003/0139751 A1 | 7/2003 | Evans et al. | |
| 2004/0006365 A1 | 1/2004 | Brady et al. | |
| 2004/0015151 A1 * | 1/2004 | Chambers | 604/532 |
| 2004/0254602 A1 | 12/2004 | Lehe et al. | |
| 2005/0277976 A1 | 12/2005 | Galdonik et al. | |
| 2006/0129091 A1 | 6/2006 | Bonnette et al. | |
| 2006/0200191 A1 | 9/2006 | Zadno-Azizi | |
| 2007/0060908 A1 | 3/2007 | Webster et al. | |
| 2007/0060944 A1 * | 3/2007 | Boldenow et al. | 606/200 |
| 2007/0250096 A1 | 10/2007 | Yamane et al. | |

OTHER PUBLICATIONS

Guenther et al., "Aspiration Catheter for Percutaneous Thrombectomy: Clinical Results," *Radiology* Apr. 1990 175(1):271-273.

Nakagawa et al., "A Retrievable Nitinol Vena Cava Filter: Experimental and Initial Clinical Results," *J. of Vascular and Interventional Radiology*, May-Jun. 1994; 5:507-512.

Reeder et al., "Aspiration Thrombectomy for Removal of Coronary Thrombosis," *American Journal of Cardiology*, Jul. 1, 1992 70: 107-110.

Search Report for European Patent Application No. 06813517.7, dated Nov. 30, 2010.

\* cited by examiner

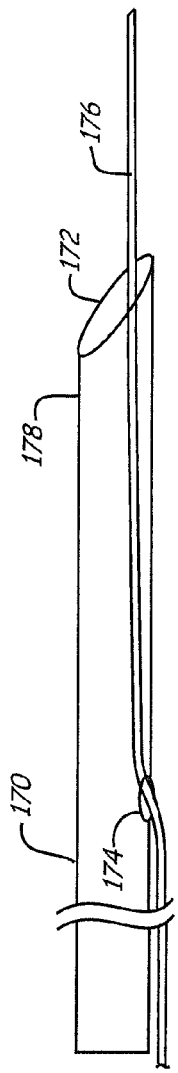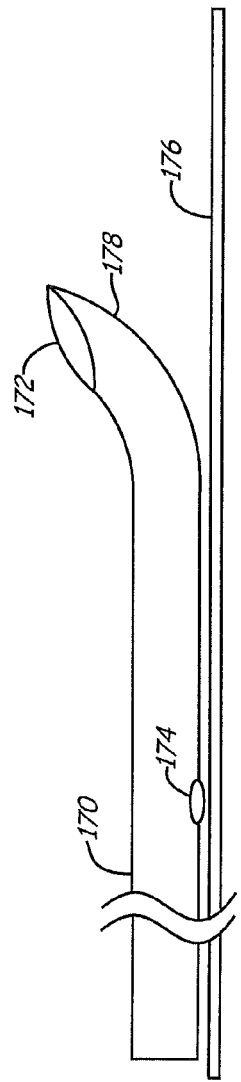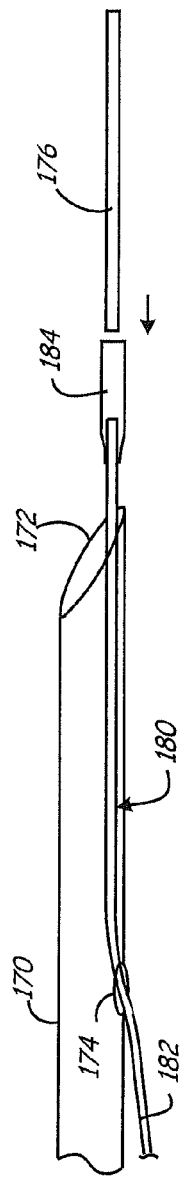

RAPID EXCHANGE CATHETER

CROSS REFERENCE TO RELATED APPLICATIONS

This application is a continuation of U.S. patent application Ser. No. 11/206,680, filed on Aug. 18, 2005, to Webster et al., entitled "Thrombectomy Catheter," incorporated herein by reference.

FIELD OF THE INVENTION

The invention relates to a thrombectomy or vascular aspiration catheter having modifications that significantly facilitate the performance of a thrombectomy within a patient's vessel. The invention further relates to procedures for performing a thrombectomy using improved catheter designs.

BACKGROUND OF THE INVENTION

An embolus can be any particle comprising a foreign and/or native material, which enters the vascular system or other vessel of the body with potential to cause occlusion of blood flow. Emboli can be formed from aggregates of fibrin, blood cells or fragments thereof, collagen, cholesterol, plaque, fat, calcified plaque, bubbles, arterial tissue, and/or other miscellaneous fragments or combinations thereof. Emboli can lodge in the narrowing regions of medium or small sized blood vessels that feed the major organs. Loss of blood flow to surrounding tissue causes localized cell death or infarction. Cerebral infarcts can cause stroke leading to confusion, disturbance of speech, paralysis, visual disturbances, balance disturbances and even death. In the heart, emboli can cause myocardial infarcts, i.e. heart attacks. Myocardial infarction refers to the death of a section of myocardium or heart muscle. Myocardial infarction can result from at least partial blockage of the coronary artery or its branches. Blockage of capillaries associated with the coronary arteries can result in corresponding microinfarctions/microinfarcs. The resulting impairment may be short term or permanent.

In some contexts, thrombus has been used to refer specifically to clots generally comprising fibrin and/or platelets. However, as used herein with respect to removal from a vessel, thrombus is used broadly to refer to any debris within a vessel that restricts or potentially restricts flow. Thus, thrombus is used interchangeably with debris and with emboli. Thrombus can result in undesirable restriction of flow within the vessel. In addition, release of thrombus from a particular location can result in a more serious blockage of flow downstream from the initial release location. Foreign material in the stream of flow can cause turbulence or reduced flow. Such flow conditions have been shown to increase rates of infection. Thrombus not only restricts flow, but also increases the risk of infection.

Disease states including, for example, arteriosclerosis and deep vein thrombosis, aging and even pregnancy can cause build up of plaque and fibrin on vessel walls. Anything that loosens or breaks up this plaque can generate emboli/thrombus. The clinical ramifications of emboli are staggering. Emboli generated from arteriosclerosis of the carotid artery alone cause 25% of the 500,000 strokes that occur yearly in the United States (2002 American Heart Association And Stroke annual statistics).

Ironically, percutaneous and surgical interventions used to remove or bypass the plaque of arteriosclerosis (e.g., balloon dilatation angioplasty, endarterectomy, bypass grafting and stenting) can themselves disrupt plaque. One of the most common cardiovascular interventions is coronary artery bypass grafting (CABG). Historically, 10-20% of all percutaneous coronary interventions in bypass grafts generate emboli large enough to cause myocardial infarcts. This is particularly true when the graft used is of saphenous vein origin. Other procedures also have the potential to generate emboli. In fact, doppler ultrasound shows evidence of microembolization in almost all cardiac and carotid intervention cases. Of the over 1.8 million intervention procedures performed annually, greater than 10% result in neurocognitive disturbance and/or ischemic events. These impairments are frequently short term, but can be permanent.

Percutaneous interventional procedures and surgical procedures for the treatment of renal artery stenosis can also generate emboli. There is clinical evidence to suggest that 36% of those treated suffer arterioloar nephrosclerosis caused by atheroemboli. Five-year survival of patients with atheroembolic events is significantly worse than of patients without atheroemboli (54% vs. 85% respectively)[Krishmamurthi et al. J Urol. 1999, 161:1093-6].

Pulmonary embolism to the pulmonary arteries from deep veins of the legs is another major clinical problem, often with a large embolic load. Patients with the potential for pulmonary embolism may benefit from thrombus removal.

SUMMARY OF THE INVENTION

In a first aspect, the invention pertains to a thrombectomy catheter comprising a suction device, a proximal portion fluidly connected to the suction device, a tubular shaft attached at its proximal end to the proximal portion, and a tip portion at the distal end of the tubular shaft. A continuous suction lumen extends from the proximal portion to the tip portion. Furthermore, the tip portion comprises a suction port in fluid communication with the suction lumen. In some embodiments, the tip portion has a first configuration and a second configuration that is curved relative to the first configuration.

In a further aspect, the invention pertains to a thrombectomy catheter comprising a suction device, a proximal portion fluidly connected to the suction device, a tubular shaft attached at its proximal end to the proximal portion, and a tip portion at the distal end of the tubular shaft. A continuous suction lumen extends from the proximal portion to the tip portion, and the tip portion comprises a suction port in fluid communication with the suction lumen. In some embodiments, the tip portion has a curve to present a displacement from the tip's natural outer diameter of at least about 2 or 3 mm.

In another aspect, the invention pertains to a thrombectomy catheter comprising a suction device, a proximal portion fluidly connected to the suction device, a tubular shaft attached at its proximal end to the proximal portion, and a tip portion at the distal end of the tubular shaft. A continuous suction lumen extends from the proximal portion to the tip portion, and the tip portion comprises a suction port in fluid communication with the suction lumen. In some embodiments, the tip portion having a curved structure that provides at least three curved segments.

In additional aspects, the invention pertains to a method for removing thrombus from a vessel of a patient. The method comprises aspirating fluid and particulate matter from the vessel through a suction port in a thrombectomy catheter having a tubular shaft that forms a majority of the length of the catheter and a tip portion comprising the suction port. The tip portion is connected at the distal end of the shaft with an aspiration lumen extending from a suction device to the aspiration port. Also, in some embodiments, the tip portion is curved to position the suction port adjacent to a vessel wall within a distance of the vessel wall that is no more than about 10 percent of the vessel diameter. In additional embodiments, the tip portion has a displacement across the vessel at least as large as the vessel diameter such that a section of the tip portion contacts the vessel wall.

In other aspects, the invention pertains to a thrombectomy catheter comprising a suction device, a proximal portion fluidly connected to the suction device, a tubular shaft attached at its proximal end to the proximal portion, a tip portion at the distal end of the tubular shaft with a continuous suction lumen from the proximal portion to the tip portion, and a partially occluding structure. In some embodiments, the partially occluding structure can comprise a flap that extends outward from other portions of the catheter or a balloon that extends only partially around the circumference of the catheter. The tip portion comprises a suction port in fluid communication with the suction lumen.

Furthermore, the invention pertains to a method for removing thrombus from a vessel of a patient. The method comprises aspirating fluid from the vessel through a suction port in a thrombectomy catheter having a tubular shaft that forms a majority of the length of the catheter and a tip portion comprising the suction port. The tip portion is connected at the distal end of the shaft with an aspiration lumen extending from a suction device to the aspiration port. Flow is partially occluded with a partial occlusion structure that extends from the outer diameter of the catheter.

BRIEF DESCRIPTION OF THE DRAWINGS

FIG. 4A is a fragmentary side view of a rapid exchange thrombectomy catheter with a suction port at its distal end and an angled opening.

FIG. 4B is a fragmentary side view of the rapid exchange aspiration catheter of FIG. 4A shown with the guide structure separated from the aspiration catheter.

FIG. 4C is a fragmentary side view of the distal end of the rapid exchange catheter of FIG. 4A shown with a loading tool facilitating the loading of the guide structure within the rapid exchange port.

DETAILED DESCRIPTION OF THE INVENTION

Figure 1:
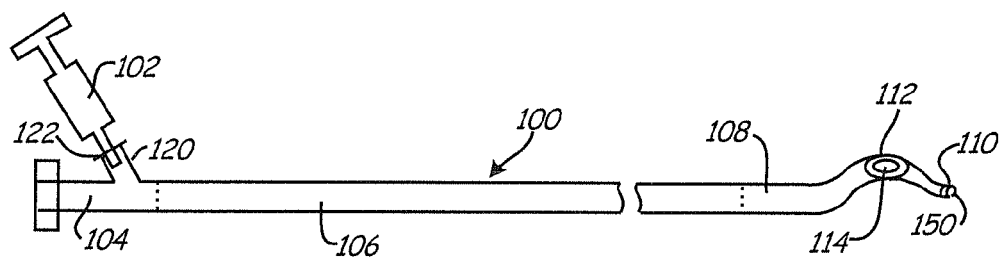
FIG. 1 is a fragmentary side view of a thrombectomy catheter with a curved tip portion.

An improved thrombectomy catheter has a curve in the catheter near its distal end and a suction port at or near the distal end of the catheter in an appropriate configuration such that the suction port can be located at or near the wall of a vessel upon deployment within a patient's vessel. Through the application of torque to the catheter, the suction port can be swept around the inner circumference of the vessel to remove effectively thrombus from various locations within the vessel, and similarly lateral motion can be used to sweep the length of the vessel to remove thrombus. Several types of curved structures can be provided for the catheter tip while providing a desired configuration for the suction port. In some embodiments, the catheter tip can be bent to a straighter configuration for delivery to the selected location within a vessel. The ability to position an aspiration port at or near a vessel wall provides for significantly improved ability to remove thrombus attached to the wall since the aspiration is directed to the thrombus where the suction can be more effective than directing the suction generally in the vicinity of the thrombus. By balancing the flexibility of the catheter tip material, the tip can be flexible enough for efficient delivery while having a sufficiently fixed configuration such that the side port can be maintained at or near the vessel wall near where the thrombus is attached.

The present devices and corresponding processes are intended for the direct removal of thrombus from a patient's vessel using suction. The thrombectomy catheters described herein can be used alone or in association with other treatment approaches. Thus, suitable deposits of thrombus can be directly removed as an alternative or in preparation for the delivery of a stent and/or other treatments. Visualization techniques can be used to position the catheter at the desired location. With more effective suction, thrombus removal can be more effective without the need for mechanical or other abrasion to loosen the thrombus and with less disruption of the natural flow through the vessel. In some embodiments, the flow can be partially occluded to increase the effectiveness of the suction.

If the thrombosis catheter is used along with other treatment approaches, the aspiration can be applied prior to or after the use of other treatment devices. For example, the thrombectomy catheter can be used prior to the application of the other treatment approach to remove dispersed sections of thrombus to better localize the thrombus prior to use of the other treatment approach. Additionally or alternatively, the thrombectomy catheter can be used after application of another treatment approach to remove residual thrombus that was not adequately treated using the initial approach. In either application, the ability to predictably place the suction port at or near the wall of the vessel improves the performance of the procedure and the control of the ultimate results.

Medical systems incorporating the thrombectomy catheter can make use of general devices and methods for the performance of less invasive percutaneous procedures. In particular, guide catheters, hemostatic valves and other devices to facilitate catheter use can be adapted for use with the present catheter systems. The specific instrumentalities for use with the thrombectomy catheters include, for example, a guide structure, an optional filter and optional additional treatment structures. Suitable guide structures include, for example, guidewires and integrated guide devices that have a corewire and an overtube, as described further below. Optional filters can comprise fibers that form a three-dimensional filtration matrix and can be adapted for deployment using an integrated guiding device. Optional additional treatment structures include, for example, angioplasty balloons, stents, and abrasion-based thrombectomy structures.

The thrombectomy catheters described herein are aspiration catheters adapted to more effectively aspirate adjacent a vessel wall. The thrombectomy catheters can have an over-the-wire design or a rapid exchange design. In an over-the-wire design, the catheter is designed such that the guide structure traverses from a point near the proximal end of the catheter to a point near the distal end of the catheter within the catheter. In a rapid exchange design, the guide structure lies outside of the catheter except for a rapid exchange segment near or at the distal end of the catheter. The guide structure extends within at least a portion of the rapid exchange segment. Functional features relating to the delivery of suction and the orientation and structure of the distal tip of the catheter are generally independent of the over-the-wire versus rapid exchange structure, although some minor design considerations may be influenced by the rapid exchange nature of a particular device.

In general, the thrombectomy catheters comprise a suction device, a proximal portion connected to the suction device, a tubular shaft attached at its proximal end to the proximal portion and a tip portion at the distal end of the tubular shaft. A continuous suction lumen is formed between the proximal portion and the tip portion. The continuous lumen provides for the transmission of suction from the suction device, such as a syringe, at the proximal portion to a port located in the tip portion. The suction port can be located at the distal end of the catheter or at a location displaced from the distal end such that the port can be referred to as a side port. In some embodiments, the tip portion can have a plurality of suction ports.

Regardless of the location of the suction port, the distal portion has a configuration that generally positions the port at or near the wall of the vessel for the application of suction at the vessel wall for appropriately sized vessels. Thus, the distal portion has a curved configuration to present a displacement across the vessel diameter comparable to or greater than the vessel diameter to constrain the port at or near the vessel wall generally through contact with the vessel walls at multiple points. The curve can result in a displacement of the catheter tip greater than the diameter of most vessels in which the catheter is used such that the suction port is generally adjacent to the wall of the vessel during use. A single catheter can be used for a range of vessel sizes while having a suction port appropriately positioned at or near the vessel wall.

In some embodiments, the catheter tip portion has two configurations. A first configuration is designed to facilitate delivery of the catheter at the desired site with less opportunity for interacting with features within the vessel during delivery. In particular, this delivery configuration generally has a straighter orientation with respect to an axis that runs along the tubular shaft of the device. A second configuration has a more curved orientation. In the more curved orientation, the port is displaced such that it is constrained to be close to the wall of the vessel for appropriately sized vessels. The release of the tip from the first orientation to the second curved orientation can be performed through the relative positioning of the catheter with respect to the guide structure or with a separate actuation element. The second orientation can be the natural position of the tip such that the first straighter orientation involves straining the tip to the straighter configuration. The straighter configuration is maintained until released such that it can transition to the second more bent configuration.

In alternative embodiments, the tip portion has a curve that inherently positions the port at or near the vessel wall once the catheter is placed at the selected location. The tip portion can have a plurality of curves that contour the tip to yield desired results. In particular, the tip portion has a configuration such that one edge of the tip portion is positioned near the vessel wall to constrain another portion of the tip portion to be near the opposite side of the vessel wall. A suction port can be place near one or both of these portions that are located near or at the vessel wall. While suitable configurations can be achieved with a single curve at the tip, a plurality of curves can result in desirable contours that can be directed conveniently to the target site. In some embodiments, the device has a plurality of curves and a side port.

Generally, the distal tip of the thrombectomy catheter is made from a material that is more flexible than the shaft of the catheter. The shaft generally is flexible enough to negotiate through the patient's vessels but stiff enough for control of the movement of the catheter from the proximal end. The distal tip portion or section thereof can be more flexible to provide for improved steering of the catheter as the catheter is being negotiated through a patient's vasculature or other vessels. The flexibility of the tip can also be beneficial with respect to contacting the vessel walls without inducing damage to the walls since the tip should be flexible enough that the vessel wall is not damaged from the contact with the walls.

The thrombectomy catheter can comprise a structure to induce a partial occlusion of the vessel beyond the constraints induced by the presence of the catheter shaft. The suction from the thrombectomy catheter to some degree works against the natural flow within the vessel. Avoiding total occlusion of the vessel reduces the risk to the patient that can result from the stopped flow. Also, having some flow can help to irrigate the site to provide more complete removal of thrombus. However, the full flow in the vessel can require excessive suction through the catheter and can flow dislodged thrombus from the site before suction can remove the thrombus into the catheter.

To better balance the conditions for the removal of thrombus from the vessel, partial occlusion of the vessel can be desirable. With respect to the thrombectomy catheter, it can be desirable to partially occlude by directing flow away from the suction port of the thrombectomy catheter. Through directing flow away from the suction port, the flow in the vessel tends to direct nearby thrombus into the port rather than away from the port. This turbulent flow tends to increase the effectiveness of thrombus removal rather than removing thrombus from the site of suction to defeat the objectives of the procedure.

To perform the thrombectomy, the catheter is positioned near the thrombus, generally using a suitable less invasive delivery procedure, although a surgical procedure can be used to expose the vessel. For example, generally heart procedures involve an incision in the groin or wrist to access an artery that leads to the heart. Suitable visualization approaches can be used to position the tip of the catheter. The thrombus can be located prior to and/or during the thrombectomy procedure.

Once the catheter tip is positioned in a region of thrombus, the catheter tip is curved, if it is not delivered in a curved configuration. For appropriate embodiments, suction may or may not be applied during the introduction of the catheter into the vessel and during tracking to the target position. Further, suction may or may not be applied as the tip is moved to its curved configuration. In the curved configuration, the suction port is positioned at or near the vessel wall. With suction being applied, the aspiration catheter can generally be moved to sweep the suction port along the inside of the vessel wall. The catheter tip can be moved circumferentially and/or laterally along the vessel wall. The lateral movement can be in a distal and/or a proximal direction. The extent of the motion of the catheter tip can be selected based on an evaluation of the thrombus within the vessel.

As further protection, the guide structure can comprise an embolism protection device to capture any thrombus that escapes aspiration to become emboli moving within the vessel. Suitable embolism protection devices include, for example, embolism protection devices formed from fibers that are expanded across the vessel lumen to collect emboli. An integrated guiding structure, with a corewire and overtube, can be used as the guiding apparatus for the catheter such that the integrated guiding structure can be used to deploy and recover the embolism protection device. If desired, a separate aspiration, recovery catheter can be used to facilitate recovery of the embolism protection device.

Furthermore, the thrombectomy catheter can be used in combination with other treatment structures. For example, the thrombectomy catheter can be used to remove portions of thrombus prior to the performance of an angioplasty procedure and/or the delivery of a stent. The prior removal of selected thrombus can improve the indications and expected results for the angioplasty/stent delivery. Alternatively or additionally, the thrombectomy catheter can be used, for example, following an angioplasty/stent delivery, for example, to remove thrombus that has been loosened and/or residual thrombus following the initial procedure. As a particular example, the thrombectomy catheter can be used to apply suction along the interior of a stent following delivery of the stent.

In additional or alternative embodiments, the improved thrombectomy catheter can be used prior to, at the same time or after the use of another thrombectomy instrumentality. Some thrombectomy instrumentalities deliver abrasive forces to vessel wall to dislodge thrombus. For example, these apparatuses can deliver cutting surfaces to the vessel wall to dislodge and/or fragment thrombus.

Whether used alone or in combination with another treatment structure, the improved thrombectomy catheter designs described herein provide considerable flexibility to a treating physician with respect to the removal of thrombus that is at least partially blocking flow within a patient's vessel. In embodiments of particular interest, the thrombectomy catheter has a single lumen from the hub to the tip to provide a larger inner cross section for the aspiration lumen. The ability to directly remove thrombus using aspiration adds another dimension to the selection of effective treatment approaches for serious medical conditions.

Thrombectomy Catheter Structures

The thrombectomy catheters of particular interest have a distal tip with a configuration having a curve that displaces a suction port such that the port would be positioned at or near a vessel wall when placed in a suitable vessel. Various curved structures can provide for suitable placement of the suction port, with several embodiments described below. In general, the thrombectomy catheter can be designed to perform a treatment procedure, i.e., thrombus removal, within any vessel of a patient, such as a urinary tract vessel, a reproductive tract vessel, or a vascular vessel. For convenience, the discussion below focuses on particular applications within vascular vessels, and a person of ordinary skill in the art can generalize this discussion for use in other particular vessels based on their size and location using the disclosure herein.

Referring to FIG. 1, a thrombectomy catheter 100 generally comprises a suction device 102, a proximal portion 104, a tubular shaft 106 and a distal tip portion 108. Thrombectomy catheter 100 further comprises radiopaque markers 110, 112. Marker 110 is at the distal end of the catheter, and marker 112 is located near suction port 114. Radiopaque materials for visualization are described further below. If the suction port is located at the distal tip, one marker can be used to identify this location. Additional or alternative marker placements can be used for visualization as desired.

Suitable suction devices 102 include, for example, suction device that draws a desired suction with respect to volumes in a selected period of time, such as a syringe, a pump, such as a peristaltic pump or a piston pump, a compressed bladder or the like. Proximal portion 104 generally is operably connected to suction device 102 and to the proximal end of tubular shaft 106. Proximal portion 104 can comprise a handle, ports or other convenient control structures for manipulating thrombectomy catheter 100 and/or the interface of thrombectomy catheter 100 and other intervention devices. Proximal portion 104 generally comprises an aspiration connection 120 that provides for connection of proximal portion 104 with suction device 102. Aspiration connection 120 can be placed at the proximal end or other location near the proximal end, as convenient. Generally, aspiration connection 120 can comprise a fitting 122 or the like to provide a sealed connection with suction device 102. Suitable fittings include, for example, a conventional fitting, such as an elastomeric diaphragm through which a syringe needle can be inserted or a Luer lock. Suction device 102 can be connected to aspiration connection 120, optionally with a portion of tubing or the like in some embodiments.

Tubular shaft 106 generally is connected at its proximal end to proximal portion 104. Tubular shaft 106 has an interior lumen that can transmit suction from the section device through the interior lumen. A portion of the suction lumen can pass through proximal portion 104.

Suitable ranges of dimensions of tubular shaft 106 generally depend on the particular use of the device. Three particular uses of interest include, for example, removal of thrombus from medium-sized blood vessels, such as coronary arteries to the heart, cerebral vessel to the head or distal leg vessels; removal of thrombus from larger vessels, such as the carotid, renal or iliofemoral vessels; or removal of thrombus from the pulmonary arteries to the lungs and from its branches. Tubular shaft 106 can have an approximately constant diameter, a varying diameter and/or sections with different diameters. In the embodiments for these uses, the average outer diameter of tubular shaft 106 ranges from about 0.010 inches (0.26 mm) to about 0.115 inches (3.0 mm), in further embodiments from about 0.020 inches (0.5 mm) to about 0.080 inches (2.1 mm) and in additional embodiment from about 0.030 inches (0.78 mm) to about 0.055 inches (1.4 mm). The outer diameter may or may not be constant over the length of shaft 106. For intervention into blood vessels near the heart, shaft 142 generally has a length in some embodiments from about 75 cm to about 200 cm, in additional embodiments from about 85 cm to about 180 cm, and in further embodiments from about 100 cm to about 170 cm. For the performance of carotid endarterectomy, the thrombectomy catheter generally can have a length less than 75 cm (29.5 inches), in further embodiments from 5 cm (2.0 inches) to 50 cm (19.7 inches) and in other embodiments from about 8 cm (3.1 inches) to about 40 cm (15.7 inches). A person of ordinary skill in the art will recognize that for each of the embodiments additional ranges of dimensions of the thrombectomy catheter within the explicit ranges above are contemplated and are within the present disclosure.

Two general forms of the thrombectomy catheter include, for example, an over-the-wire design or a rapid exchange design. The rapid exchange design has a port through which a guidewire/guide structure can enter into the catheter while in an over-the-wire design the guide structure travels within the catheter along the majority of the length or the entire length of the catheter within the patient. It may be somewhat arbitrary in some embodiments to specify the point at which the tip portion starts and the shaft end, but certain structure is associated with the tip portion. Also, the tip or a portion thereof is generally formed from different materials than the shaft, and this change in composition can be used to demarcate the tip from the shaft. With either an over-the-wire design or a rapid exchange design, the guide structure can travel through the suction lumen or through a separate lumen.

Figure 2:
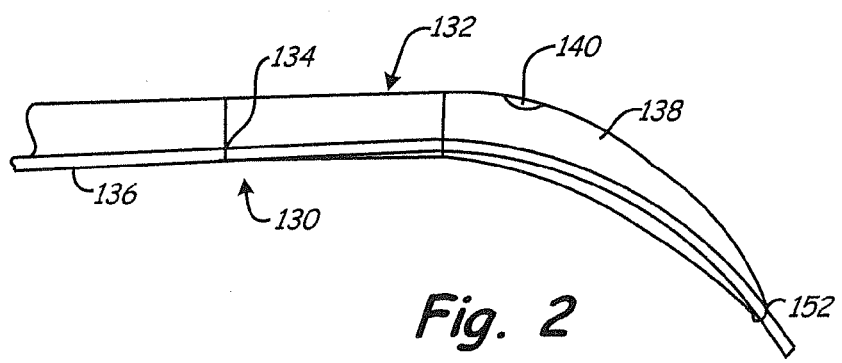
FIG. 2 is a fragmentary side view of the distal end of a thrombectomy catheter with a rapid exchange segment.

A catheter with a rapid exchange design has a rapid exchange segment that comprises the distal tip portion. Referring to FIG. 2, catheter 130 has rapid exchange segment 132 and a guide port 134 through which guide structure 136 can pass. A standard guidewire for vascular applications has a diameter of about 0.014 inches, such that a suitable port would be slightly larger, such as 0.0145 inches, to provide for passage of the guide structure. Distal tip portion 138 comprises a side suction port 140. The positioning of the guide port can be selected at least in part based on the curve of the tip and the position of the suction port. For example, if the catheter has a side suction port, the guide port can be located along the opposite side of the tubular structure, as shown in FIG. 2, which can be advantageous for loading the rapid exchange segment onto a guide structure with embodiment in which the guide structure travels within the suction lumen. Furthermore, a tube or other loading tool can be preloaded through guide port 134 to facilitate loading of the guide structure into the guide port from the distal opening when the guide structure is placed within the patient. The loading tube or loading tool can be removed once the guide structure is guided through guide port 134. Many of the designs below can be adapted for a rapid exchange configuration through the inclusion of a suitable guide port.

For embodiments with a side suction port, the tip of the catheter can be tapered to have a guide exit port effectively at the distal end of the catheter. These tip structures can be applicable to either a rapid exchange design or an over-the-wire design. Referring to FIG. 1, guide exit port 150 is located at the distal end of distal tip portion 108. Similarly, referring to FIG. 2, guide exit port 152 is located at the distal end of rapid exchange segment 132. The tapering of the catheter end with the exit port effectively blocks suction through the end of the tip portion since the guide structure blocks the exit port such that suction effectively is directed only to the suction port. However, in some embodiments multiple suction ports can be used, such as two side ports or a side port and a distal end port.

Figure 3A:
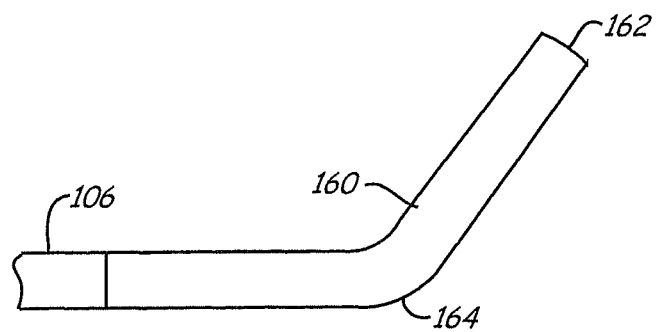
FIG. 3A is a fragmentary side view of the distal end of a thrombectomy catheter with a suction port at its distal end.
Figure 3B:
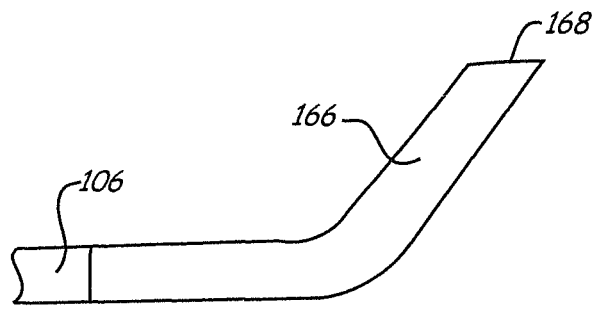
FIG. 3B is a fragmentary side view of a distal end of a thrombectomy catheter with a suction port at its distal end having an angled opening relative to its lumen.

In further embodiments, the suction port is located at the end of the distal tip portion. Referring to FIG. 3A, distal tip portion 160 extends from shaft 106. Distal tip portion 160 has a suction port 162 at its distal end. A rapid exchange segment can similarly have a suction port at its distal end. In either embodiment, the guide structure generally extends out from the catheter at the distal end, although it extends traverse along the length of the catheter shaft within the aspiration lumen or through a separate guide lumen. As shown in FIG. 3A, distal tip portion 160 has a curve 164 that tends to position suction port 164 at the vessel wall when the catheter is within a patient's vessel. As shown in FIG. 3A, the end of distal tip portion has an orientation that is essentially perpendicular to the axis of the lumen. In an alternative embodiment shown in FIG. 3B, distal tip portion 166 has a suction port 168 at the end of distal tip portion 166 that is at an angle to the axis of the lumen. The angle can orient the port more level along the wall of the vessel to facilitate the application of suction along the wall.

A rapid exchange embodiment of a thrombectomy catheter with a distal suction port is shown in FIG. 4A. Thrombectomy catheter 170 has suction port 172 with an angled opening at its distal end and a guide port 174. For delivery, guide structure 176 extends through guide port 174 and out through suction port 172. Distal tip 178 of thrombectomy catheter 170 has a natural curved shape as seen in FIG. 4B. Referring to FIG. 4A, flexibility of distal tip 178 tends to conform distal tip 178 to the path of the guide structure 176. To free distal tip 178 to follow its natural curved configuration for performing the thrombectomy, guide structure 176 can be withdrawn through guide port 174. Guide structure can be returned to its original position for subsequent use, as shown in FIG. 4B, or guide structure 176 can be withdrawn from the patient.

Figure 4D:
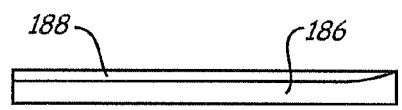
FIG. 4D is a side view of an alternative embodiment of a loading tool.
Figure 4E:
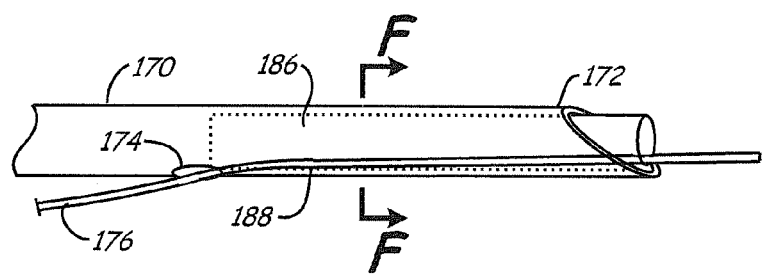
FIG. 4E is a fragmentary side view of the distal end of the rapid exchange catheter of FIG. 4A shown with the loading tool of FIG. 4D.
Figure 4F:
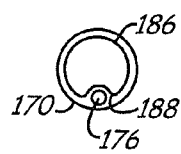
FIG. 4f is a sectional view of the catheter and loading tool of FIG. 4E taken along line F-F of FIG. 4E.

Referring to FIG. 4C, a loading tool 180 can be used to facilitate the placement of guide structure 176 through guide port 174. Loading tool 180 comprises a rod 182 and a tube 184, such as a polymer tube. The end of guide structure 176 can be held within tube 184 and pulled through guide port 174. Loading tool 180 can be removed after the guide structure is loaded. An alternative embodiment of a loading tool is shown in FIG. 4D. Loading tool 186 fits within the suction port 172. Loading tool 186 has a generally cylindrical shape with a channel 188 extending along one side. With the loading tool within suction port 172, channel 186 can direct guide structure 176 to guide port 174, as shown FIG. 4E. A sectional view of the guide structure within channel 186 is shown in FIG. 4F.

Figure 5:
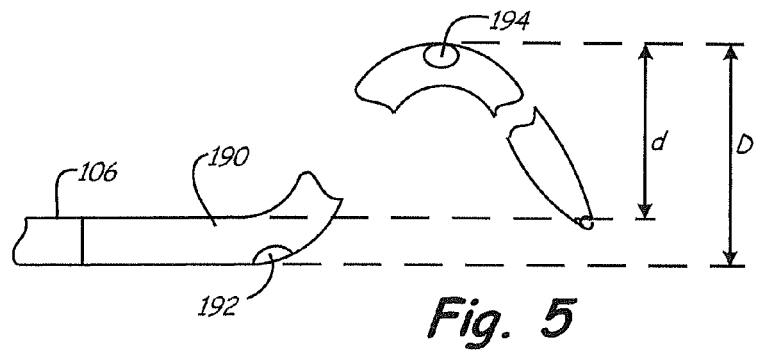
FIG. 5 is a fragmentary side view of a distal end of a curved tip of a thrombectomy catheter with displacement distance "D" marked appropriately.

The curved distal tip portion generally is configured to direct the suction port at or near the vessel wall. Generally, this positioning is accomplished through having a sufficient bend in the catheter tip that the suction port and another portion of the catheter along its natural position are displaced from each other at least by roughly the diameter of the vessel such that the suction port necessarily is at or near the vessel wall. This is shown schematically in a fragmentary view in FIG. 5. Distal tip portion 190 has one or more curves. Several specific embodiments for the curved portion are presented above and below. As shown in FIG. 5, distal tip portion can have suction ports 192 and/or 194 near the extremes in the displacement of the device. Suction port 194 can be a side port or a port at the distal end of the catheter tip, although the ports are shown as side ports in FIG. 5.

Relative to the axis that runs along shaft 106 of the catheter, the curved distal tip portion 190 has a perpendicular displacement "D" as shown in FIG. 5. Displacement "D" corresponds with the distance that the tip naturally extends without constraints imposed by the vessel such that it is largest extent across the vessel that the distal tip portion can extends. Thus, if "D" is greater than or close to the vessel diameter, suction ports 192 and 194 are at or near the vessel wall. For many embodiments, "D" is greater than the diameter of the corresponding vessel such that the tip portion is bent from contact with the vessel wall that effectively constrains the displacement of the curved tip portion to a value less than "D." Also, "D" involves a displacement beyond the natural outer diameter of the catheter "d" which is also depicted in FIG. 5.

In practice, catheters with one or more selected displacements "D" generally are used for commercial distribution such that a physician can select the appropriate sized catheter for the vessel. In some embodiments, the tips are one-size-fits-all for a particular vessel type, such as coronary arteries. For these embodiments, "D" is selected to be as large or larger than the largest vessel diameter that is anticipated for use of the device. Thus, in most vessels with appropriately sized catheters, the tip is distorted by contact with the vessel wall. The distal tip portion can be formed from a material that is flexible enough such that the contact with the vessel wall does not damage the vessel wall. In further embodiments, a set of different tip sizes can be sold such that each design is intended for use in vessel over a range of sizes. However, anticipated contact with the vessel wall for the selected catheter size can ensure that the suction port is at or near the vessel wall.

In some embodiments directed to coronary arteries (generally with diameters from about 2 to about 7 mm), D can be selected to be at least about 7.5 mm, and in further embodiments to be about 7.0 mm. For embodiments directed to carotid arteries and other vessels of similar caliber (generally with diameters from about 6 to about 10 mm), D can be selected to be at least about 11 mm and in further embodiments to be about 10 mm. For embodiments directed to use in the aorta (generally with diameters from about 20 to about 35 mm), D can be selected to be at least about 40 mm and in further embodiments to be about 35 mm. With respect to the displacement beyond the natural outer diameter of the catheter, "d" can be at least about 2 mm, in further embodiments, at least about 4 mm, and in other embodiments at least about 5 mm. A person of ordinary skill in the art will recognize that additional ranges and values of D and d within the explicit ranges above are contemplated and are within the present disclosure. Alternatively, more specific sizes can be provided that are more specifically matched to a particular vessel size.

Figure 6A:
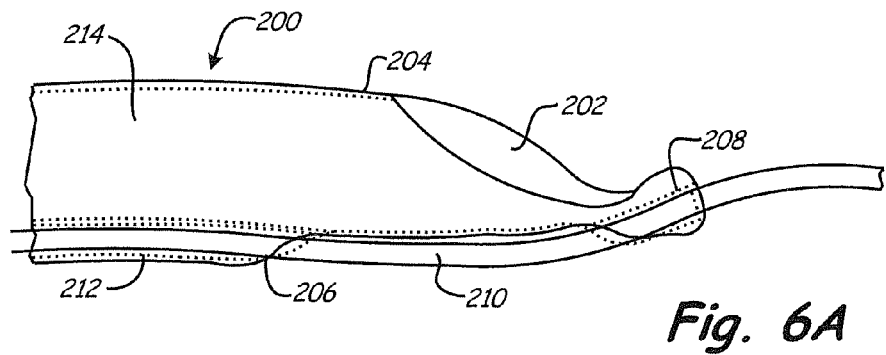
FIG. 6A is a fragmentary side view of an embodiment of the distal end of a thrombectomy catheter with a distal guide lumen and a guide structure extended through the distal guide lumen to hold the tip in a delivery configuration.
Figure 7A:
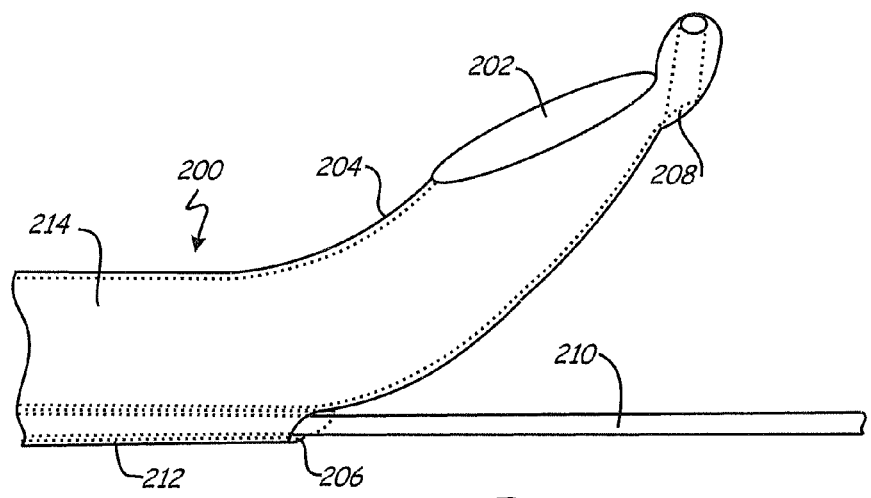
FIG. 7A is a fragmentary side view of the thrombectomy catheter of FIG. 6 with the tip in a curved configuration with the distal guide lumen free of the guide structure.
Figure 7B:
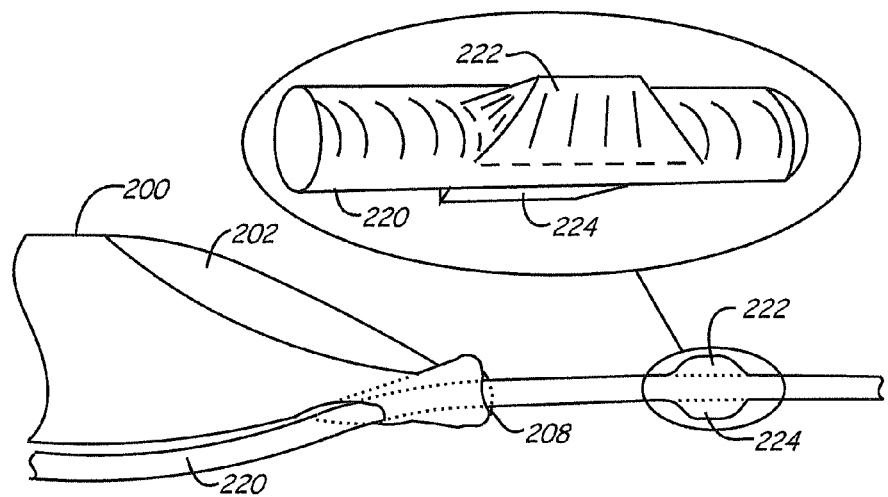
FIG. 7B is a fragmentary side view of the thrombectomy catheter of FIG. 6 with a guide structure having blades suitable to free the guide structure from the distal lumen. The insert shows an expanded view of the guide structure in the vicinity of the blades.
Figure 8:
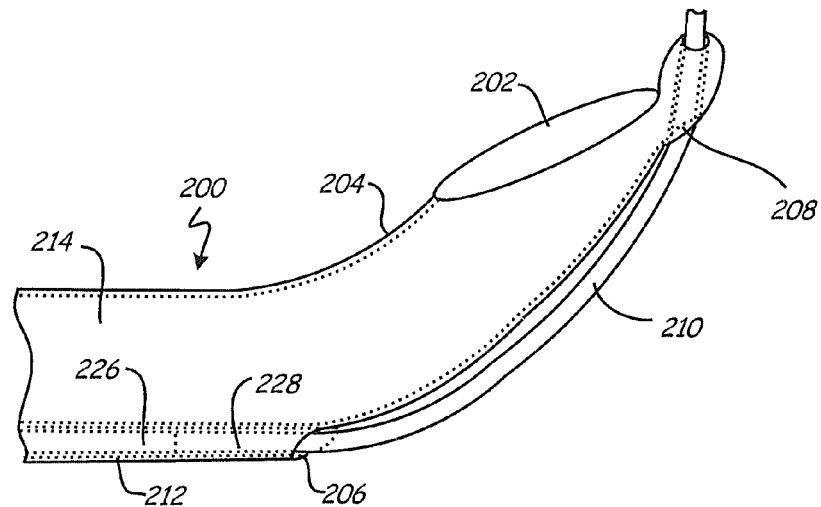
FIG. 8 is a fragmentary side view of the thrombectomy catheter of FIG. 6 with the tip in a curved configuration due to the guide structure being positioned with a flexible portion at the catheter tip.

A specific embodiment is shown in FIGS. 6-8 having a delivery configuration and a distinct curved configuration. For this catheter, the distal tip portion 200 has an angled distal aspiration port 202, a curved flexible end section 204, a guide structure exit port 206 and a distal guide structure lumen 208 that accommodates guide structure 210. As shown in FIG. 6A, guide structure 210 is located in a guide lumen 212 along most of the length of the catheter, although alternatively guide structure 210 can be designed with the guide structure located within the suction lumen 214.

Figure 6B:
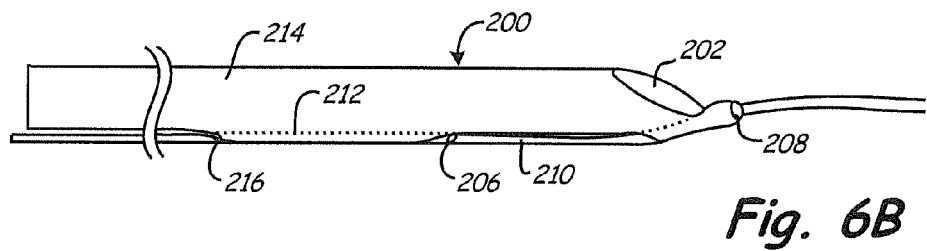
FIG. 6B is a fragmentary side view of the distal end of a rapid exchange embodiment of a thrombectomy catheter with a distal guide lumen.
Figure 6C:
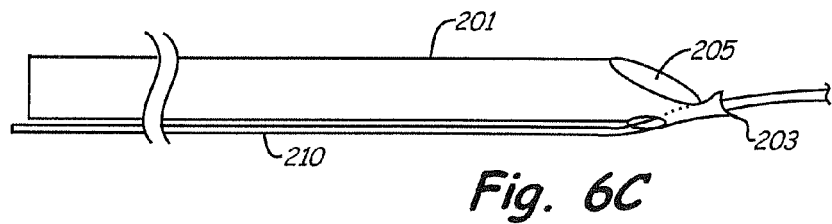
FIG. 6C is a fragmentary side view of the distal end of a thrombectomy catheter with a distal guide lumen that also functions as a rapid exchange segment.

The delivery configuration is shown in FIG. 6A. In this configuration, guide structure 210 extends outward through exit port 206 and through distal lumen 208. Guide structure 210, or an appropriate portion thereof, can be stiff enough to hold end section 204 relatively straight to facilitate passage of distal tip portion 200 to the selected location within the patient, while being flexible enough to provide for passage through a curving and branching network of vessels. FIG. 6A is consistent with an over the wire configuration. In an alternative embodiment, the catheter can be a rapid exchange configuration, as shown in FIG. 6B. In this configuration, guide structure 210 also passes through guide port 216 such that guide structure 210 is associated with catheter 200 between guide ports 206 and 216 as well as with distal guide lumen 208. In a further alternative embodiment shown in FIG. 6C, guide structure 210 associates with thrombectomy catheter 201 through a distal guide lumen 203 adjacent distal suction port 205.

A curved configuration of the device of FIG. 6A is shown in FIG. 7A. In this configuration, guide structure 210 exits through exit port 206 but does not pass through distal lumen 208. Since curved flexible end section 204 is unconstrained in this configuration, end section 204 resumes its natural curved structure, although this may be somewhat constrained by a patient's vessel when it is located within a vessel. To deploy this configuration, generally the distal tip portion 200 is positioned at the desired location within a patient. Then, the guide structure 210 is withdrawn past distal lumen 208 to free end section 204. After end section is freed, the guide structure may or may not be advanced in a distal direction to ensure that guide structure continues to exit port 206 while the catheter is moved during aspiration. Similar approaches can be used for embodiments in FIGS. 6B and 6C. Alternatively, a guide structure 220 can be formed with blades 222, 224, as shown in FIG. 7B. As blades 222, 224 are drawn into distal guide lumen, the blades cut through the structure, and the guide structure is released from the distal guide lumen such that the thrombectomy catheter assumes its curved configuration as shown in FIG. 7A. The blades can be used cut the distal guide lumen for any of the embodiments in FIGS. 6A-6C. The number, shape and position of one or more blades can be selected appropriately by a person or ordinary skill in the art based on this description.

An alternative embodiment of a thrombectomy catheter configuration is shown in FIG. 8. In this configuration, guide structure 210 comprises a first material 226 and a second material 228 in which first material 226 is less flexible than second material. In general, the guide structure as depicted in FIGS. 7A and 7B can similarly have materials with different flexibilities, but this structure of the guide structure is not relied upon to obtain the curved configuration shown in FIG. 7A. As shown in FIG. 8, if first material 226 is withdrawn into exit port 206, curved flexible end section 204 bends since the force needed to maintain end section 204 relatively straight is greater than the force needed to keep in a straight orientation second material 228 of guide structure 210.

Figure 9A:
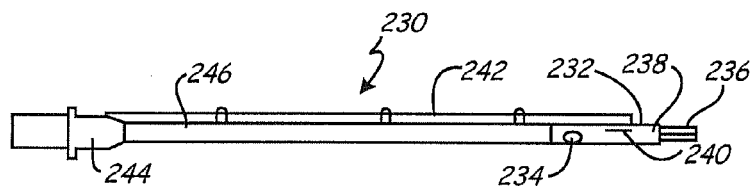
FIG. 9A is a side view of an alternative embodiment of a thrombectomy catheter with an obturator maintaining the tip in a delivery configuration.
Figure 9B:
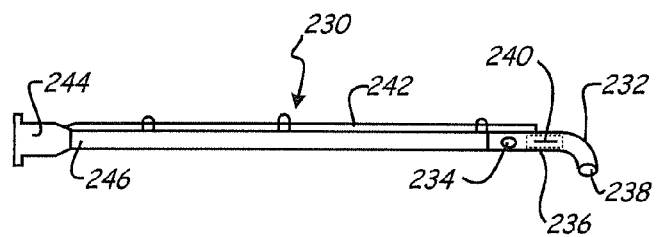
FIG. 9B is a side view of the thrombectomy catheter of FIG. 9B with the obturator withdrawn such that the tip is in a curved configuration.

Another embodiment of a thrombectomy catheter having a tip portion with two configurations is shown in FIGS. 9A and 9B. In this embodiment, thrombectomy catheter 230 comprises a curved flexible tip portion 232 with a rapid exchange port 234. Obturator 236 is a structure that is more rigid than tip portion 232. Obturator 236 can slide relative to suction port 238 at the distal end of tip portion 232. When extended, obturator 236 holds tip portion 232 in a straighter configuration. When retracted, the unconstrained tip portion 232 assumes its unrestrained curved configuration. An extended obturator 236 is depicted in FIG. 9A while catheter 230 with a retracted obturator is depicted in FIG. 9B where tip portion 232 has its natural curve. Obturator 236 is connected to a lever 238 projecting through slit 240. Lever 238 is connected to wire 242. As shown in FIGS. 9A and 9B, wire 242 passes along the exterior of catheter 230 to its proximal end 244. However, in alternative or additional embodiments, wire 242 can extend within catheter 230, such as through the suction lumen 246. A suitable obturator 236 can be, for example, a cylindrical tubular element that can slide within the lumen of tip portion 232.

Figure 10A:
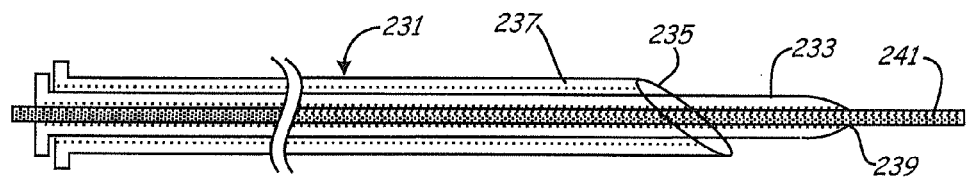
FIG. 10A is a side view of a thrombectomy catheter with an extended obturator within the lumen of the catheter.
Figure 10B:
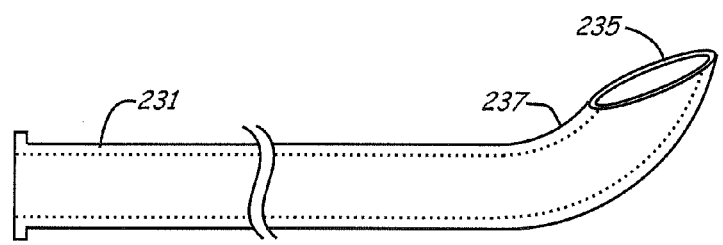
FIG. 10B is a side view of the thrombectomy catheter of FIG. 10A with a curved tip flowing removal of the obturator and guide structure.

Referring to FIG. 10A, an alternative embodiment of a thrombectomy catheter 231 with an obturator 233 that extends along the length of the catheter. The obturator can fill a substantial fraction of the suction lumen of the thrombectomy catheter, although the obturator may or may not have a roughly constant diameter over its length. Thrombectomy catheter 231 has an angled cut opening 235 at its distal end. thrombectomy catheter 231 has a curved tip 237 that is held in a straight configuration by obturator 233 for delivery into the patient. Obturator 233 has a guide lumen 239 such that obturator 233 can ride over guide structure 241 for delivery into the patient. For use, generally obturator 233 and guide structure 241 are removed. With the obturator removed, thrombectomy catheter 231 assumes its natural configuration with curved tip 237, as shown in FIG. 10B. Obturator 233 can have similar flexibility and can be formed from similar materials as catheter 231.

Figure 10C:
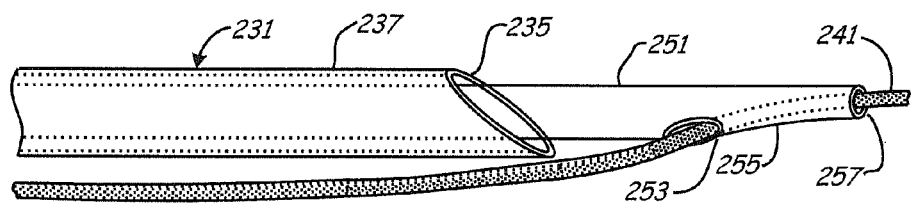
FIG. 10C is a side view of an alternative embodiment of the obturator of FIG. 10A with a rapid exchange design.

A rapid exchange obturator 251 is shown in FIG. 10C being used with thrombectomy catheter 231. In this embodiment, obturator 251 has a guide port 253 and a tapered tip 255 with a distal guide port 257. Thus, obturator 251 rides over guide structure 241 with the guide structure extending between distal guide port 257 and side guide port 253. Upon removal of guide structure 241 and obturator 251, aspiration catheter 231 again assumes a configuration with a curved tip as shown in FIG. 10B. In this embodiment, guide structure 241 can be withdrawn sufficient to release obturator 251 while being left in the patient for additional purposes. A loading tool can be used to facilitate placement of the guidewire through guide port 253.

Figure 10D:
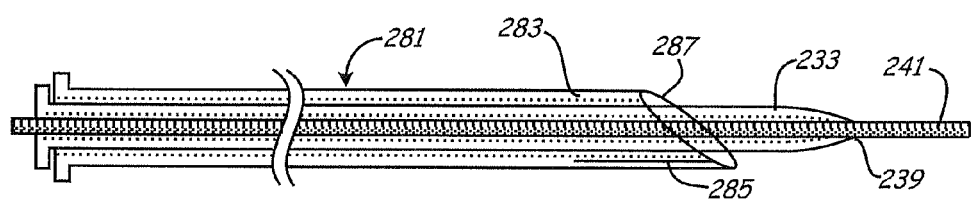
FIG. 10D is a side view of another alternative embodiment with the use of an obturator of FIG. 10A with a catheter adapted for use with a guidewire extending through a slit when the catheter tip is bent.
Figure 10E:
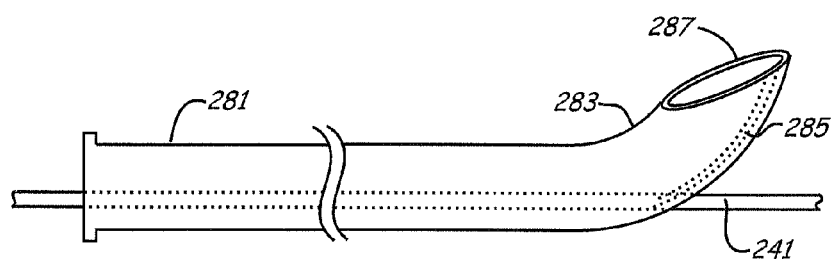
FIG. 10E is a side view of the catheter of FIG. 10D with the obturator removed such that the tip is in its curved configuration.

An embodiment of a thrombectomy catheter similar as the embodiment in FIG. 10A is shown in FIGS. 10D and 10E in which the catheter can be used with a guide structure after the obturator is removed. Referring to FIG. 10D, thrombectomy catheter 281 is used with obturator 233 and guide structure 241. Aspiration catheter 281 has a curved tip 283 that is held straight by obturator 233 for deployment. Catheter 281 also has a slit 285 extending from distal aspiration opening 287. As shown in FIG. 10E, guide structure can extend through slit 285 to extend from aspiration catheter 281 when curved tip 283 is in its natural curved configuration. Curved tip 283 can be formed with an embedded spring metal such as Nitinol® or an elastic polymer such that slit 285 remains essentially closed except near the position at which guide structure 241 extends through slit 285.

Figure 11A:
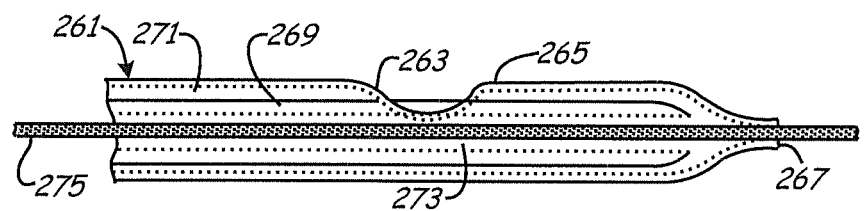
FIG. 11A is a fragmentary, side view of an alternative embodiment of a thrombectomy catheter with a side aspiration hole and with an obturator configuring the catheter for delivery.
Figure 11B:
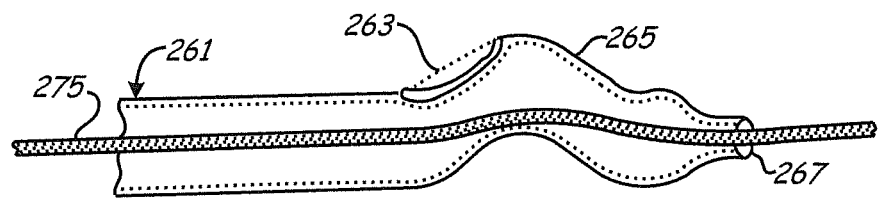
FIG. 11B is a fragmentary side view of the thrombectomy catheter of FIG. 11A with the obturator removed such that the catheter has a curved configuration.

An alternative embodiment of a thrombectomy catheter with an obturator for delivery is shown in FIGS. 11A and 11B. Thrombectomy catheter 261 has a side aspiration port 263 along a curved segment 265. The distal tip of thrombectomy catheter 261 tapers to a distal guide port 267. Obturator 269 fits within suction lumen 271 of catheter 261. Obturator 269 straightens curved segment 265 for delivery. Obturator 269 comprises a guide lumen 273 for a guide structure 275. For delivery of thrombectomy catheter 261, guide structure 275 extends from guide port 267 and through guide lumen 273. Upon removal of obturator 269, curved segment 265 resumes its natural curved configuration, as shown in FIG. 11B, which is the appropriate configuration for performing the thrombectomy procedure. In the curved configuration, the guide structure may or may not be left in place.

Figure 12A:
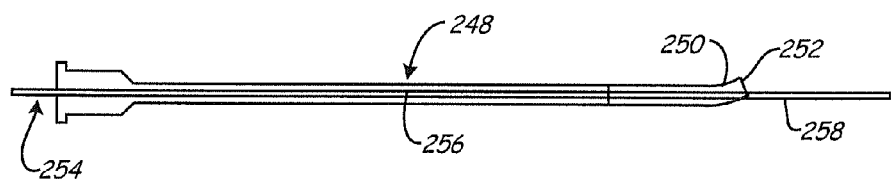
FIG. 12A is a side view of a thrombectomy catheter with a curved tip that is held in a delivery configuration by a guide structure.
Figure 12B:
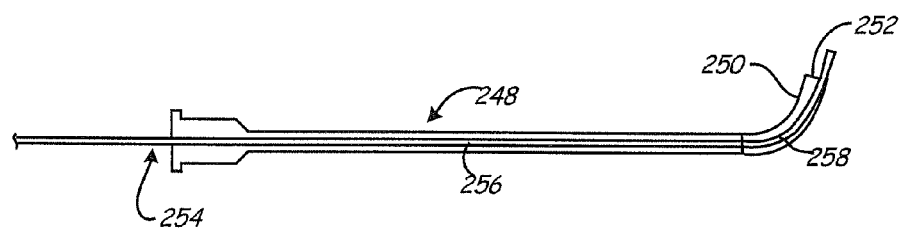
FIG. 12B is a side view of the thrombectomy catheter of FIG. 12A in which the guide structure is moved in a proximal direction to position a more flexible portion of the guide structure at the curve of the catheter such that the catheter takes it curved configuration.

A further embodiment of a thrombectomy catheter with two configurations is shown in FIGS. 12A and 12B. This embodiment is similar to the embodiment in FIGS. 10A and 10B except that the guide structure itself functions as an obturator. Referring to FIGS. 12A and 12B, catheter 248 comprises a curved flexible tip portion 250 with a suction port 252 at the distal end of tip portion 250. Guide structure 254 comprises a stiffer portion 256 and a more flexible portion 258. As shown in FIG. 12A, when guide structure 254 is extended sufficiently in a distal direction, the stiffer portion 256 of guide structure 254 along with the inertia of the guide structure extending from the suction port 252 distorts the curved tip portion into a relatively straight configuration. As shown in FIG. 12B, when guide structure is moved in a proximal direction, more flexible portion 250 is aligned with the curved portion 250 of catheter 248 such that the curve can approximately assume its natural curved configuration.

Figure 13:
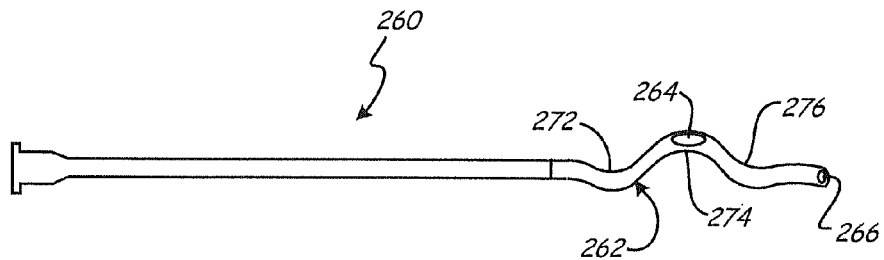
FIG. 13 is a side view of another alternative embodiment of a thrombectomy catheter with three curves of the tip and a side suction port.

As noted above, in some embodiments the thrombectomy catheter has a curved configuration without structural features to straighten the device during placement. Such an embodiment is shown in FIG. 13. Thrombectomy catheter 260 has a curved tip portion 262 with a side suction port 264 and a guide exit port 266 at end of the catheter. Tip portion 262 has three curves 272, 274, 276. Suction port 264 is located along curve 274 such that the suction port can be is positioned at or near the wall of the vessel within the patient. Suction port could be similarly places along curve 272 or 276. While the tip portion is shown with three curves, in other embodiments, the tip portion has two curves (FIGS. 1 and 2), four curves or more than four curves. Tip portion 262 generally is sufficiently flexible to provide for the placement of tip portion 262 without difficulties from the curves. While this embodiment is shown as an over-the-wire design, a comparable device can be formed with a rapid exchange design.

Figure 14A:
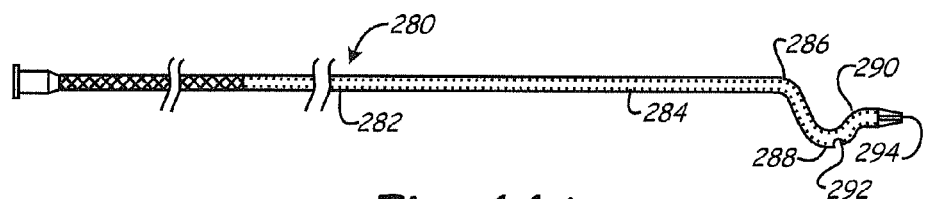
FIG. 14A is a side view of a specific embodiment of a thrombectomy catheter with three curves.

Another specific embodiment with three curves is shown in FIG. 14A. In this embodiment, thrombectomy catheter 280 comprises shaft 282 and tip portion 284. Tip portion 284 has three curves 286, 288, 290. Suction port 292 is located along curve 288. A guide structure exit port 294 is located at the distal end of the catheter.

Figure 14B:
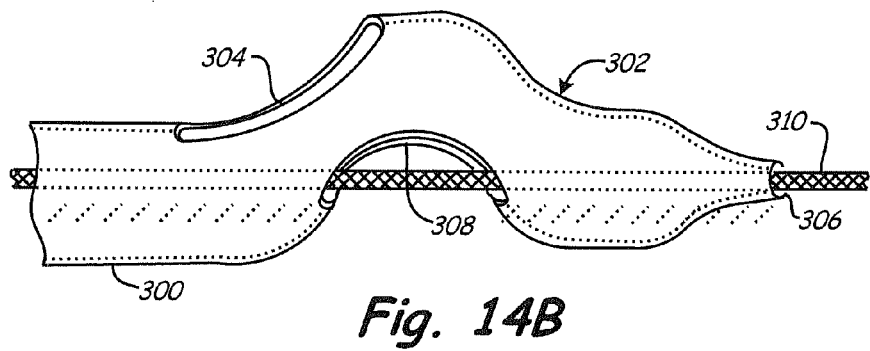
FIG. 14B is a side view of an embodiment of a thrombectomy catheter with a curved shape and a slit to provide for curving of the catheter without interference or with reduced interference of the curvature due to a guide structure associated with the catheter.

In some embodiments, the association of the thrombectomy catheter with a guide structure may interfere with a natural curvature of the catheter. This interference may be effectively used to facilitate delivery of the device, as described above with respect to FIG. 12A. However, in some embodiments, such interference may be undesirable. An embodiment of a thrombectomy catheter is shown in FIG. 14B that avoids unwanted interference with the curvature of the catheter as a result of association with a guide structure. Catheter 300 has a curved tip 302 with an aspiration opening 304 and a distal guide port 306. Curved tip 302 has the form of a bump with aspiration opening 304 along a proximal edge of the upper surface of the bump and a slit 308 along the lower surface of the bump. A guide structure 310 passes through distal guide port 306 and exits the catheter along slit 308 such that the curvature is not significantly distorted due to forces from the guide structure. Thrombectomy catheter 300 can be deployed with an obturator or other of the structures described herein to facilitate delivery.

Figure 14C:
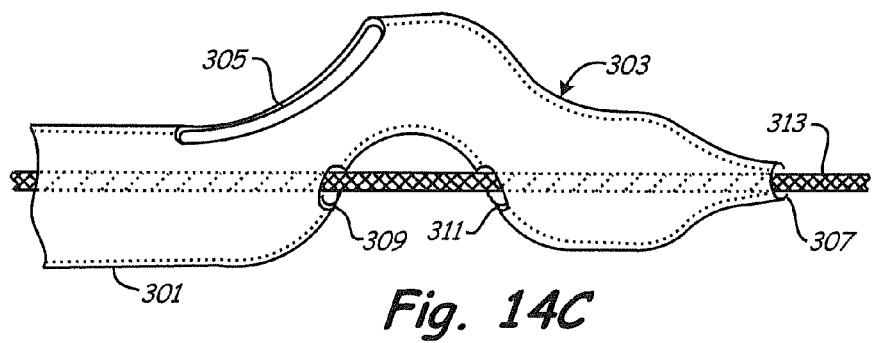
FIG. 14C is a side view of an embodiment of a thrombectomy catheter with a curved shape and with two guide ports to provide for curving of the catheter without interference or with reduced interference of the curvature due to a guide structure associated with the catheter.

A similar embodiment is shown in FIG. 14C. Thrombectomy catheter 301 has a curved tip 303 with an aspiration opening 305 and a distal guide port 307. Thrombectomy catheter 301 has two guide ports 309, 311 as a substitute for slit 308 of thrombectomy catheter 300 in FIG. 14B. Guide structure 313 passes through guide ports 309, 311 and distal guide port 307 such that thrombectomy catheter 301 can remain associated with guide structure 313 without significant interference with the natural curve of curved tip 303. Thrombectomy catheter 301 can also be delivered with an obturator or other structure to facilitate delivery.

Figure 14D:
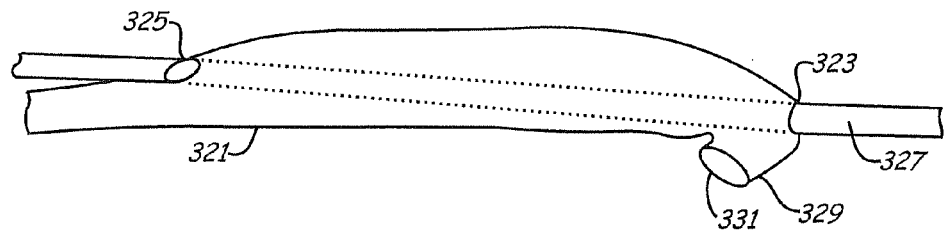
FIG. 14D is a side view of an embodiment of a thrombectomy catheter with an aspiration port at the distal end of a curved tip and with a distal guide port and a rapid exchange port.

Another embodiment of a thrombectomy catheter with a distal guide port and an aspiration port along a curved segment is shown in FIG. 14D. Thrombectomy catheter 321 comprises a distal guide port 323 and a rapid exchange port 325, although suitable catheter can be correspondingly formed in an over the wire format. A guide structure 327 can extend through distal guide port 323 and rapid exchange port 325, as shown in FIG. 14D. Curved suction arm 329 has an aspiration port 331 at the end of the arm. In this configuration, Guide structure 327 does not significantly interfere with suction. With this configuration, if suction arm 329 is formed from a flexible material, arm 329 generally deflects out of the way for convenient deployment while being properly positions for performing aspiration as it is moved in a proximal direction during the thrombectomy procedure.

Figure 14E:
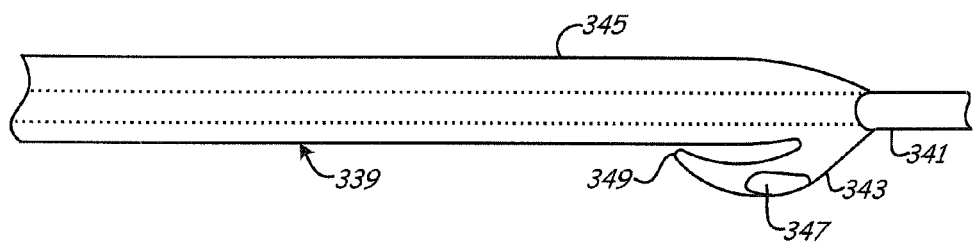
FIG. 14E is a side view of an embodiment of a thrombectomy catheter with a curved suction extension and an aspiration port along the side of the extension.

A similar embodiment is shown in FIG. 14E. Thrombectomy catheter 339 has a distal guide port through which a guide structure 341 can extend as shown in the figure. In the configuration of FIG. 14E, the catheter has an over-the-wire design, although a rapid exchange version can be formed based on the rapid exchange configurations described herein. Suction arm 343 extends from shaft 345. Suction arm 343 has a side aspiration port 347. End 349 of suction arm 343 may or may not be attached to shaft 345. Suction arm 343 can be formed from a flexible material such that it deflects during deployment of the catheter to facilitate deployment. The curvature of suction arm can be selected such that aspiration port 347 is positioned at the vessel wall during the thrombectomy procedure.

Figure 14F:
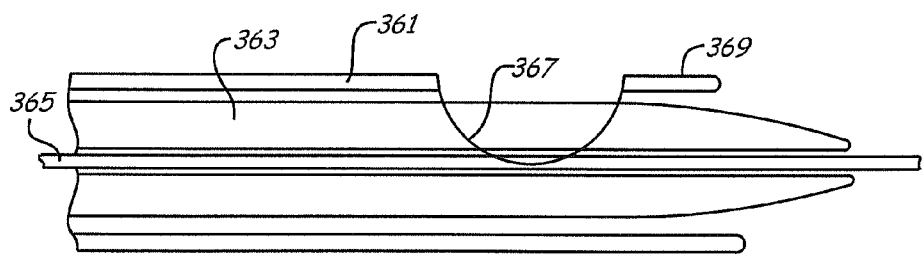
FIG. 14F is a side view of an embodiment with a flexible expandable tip.

Another alternative embodiment of the thrombectomy catheter is shown in FIG. 14F. In this embodiment, thrombectomy catheter 361 is deployed with an obturator 363 and a guide structure 365. Upon removal of obturator 363, catheter 361 takes a configuration essentially as shown in FIG. 11B with thrombectomy catheter 261. Referring to FIG. 14F, thrombectomy catheter has an aspiration opening 367 and an expandable tip 369. Obturator 363 can extend through expandable tip 369 as shown in FIG. 14F. Upon removal of obturator 363, expandable tip 369 reduces its expansion to form a guide port, such as shown in FIG. 11B, such that aspiration essentially is only performed through aspiration opening 367. Expandable tip 369 can be formed, for example, with a spring metal, such as a Nitinol®, Nitinol® embedded within a polymer, or an elastic polymer.

It may be desirable to partly occlude the flow so that the flow velocity in the vessel is reduced. Reducing the flow velocity can provide more efficient suction during the thrombectomy procedure. To achieve this partial occlusion, generally, a feature on the catheter needs to be deployed, such as actuated or inflated, to partially block flow at a location upstream and/or downstream from the suction port. A balloon mounted on the exterior of the shaft is one way to provide partial occlusion. For example, a low pressure balloon can be inflated once the catheter is tracked into position. After removal of thrombus, the balloon can be deflated and the catheter removed.

Figure 15:
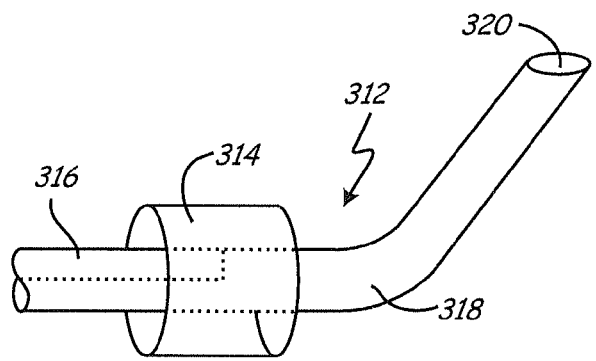
FIG. 15 is a side perspective view of thrombectomy catheter with a partially occluding balloon structure around its circumference.
Figure 16:
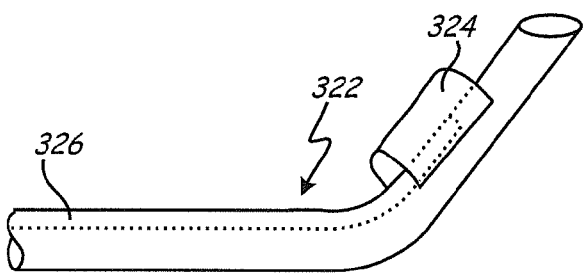
FIG. 16 is a side perspective view of a thrombectomy catheter with a partly occluding balloon element around a portion of the catheter circumference along a curve of the catheter.

One embodiment based on a balloon for partial occlusion is shown in FIG. 15. In this embodiment, aspiration catheter 312 has a balloon structure 314 around the circumference of the catheter body. A fluid, such as saline or other non-toxic fluid, can be delivered through balloon lumen 316 to inflate the balloon, and the balloon can be correspondingly deflated through removal of the fluid. The fluid can be delivered from the proximal end of the catheter, for example, using conventional approaches. Aspiration catheter 312 has a curve 318 and a distal suction opening 320. An alternative embodiment is shown in FIG. 16. Thrombectomy catheter 322 has a balloon structure 324 around a portion of the circumference of the catheter body. Balloon lumen 326 can be used to control inflation of the balloon. The size, shape and positioning of balloon structure 324 can be selected to alter the flow in the vessel as desired.

Figure 17:
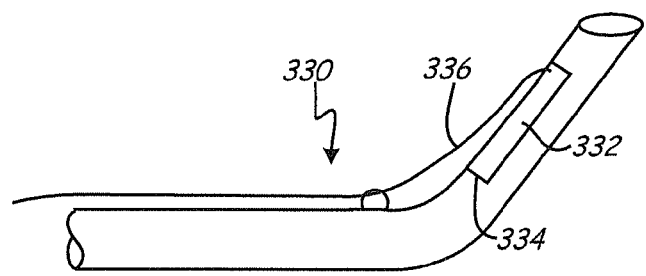
FIG. 17 is a side perspective view of a thrombectomy catheter with a partly occluding flap shown in a non-deployed configuration.
Figure 18:
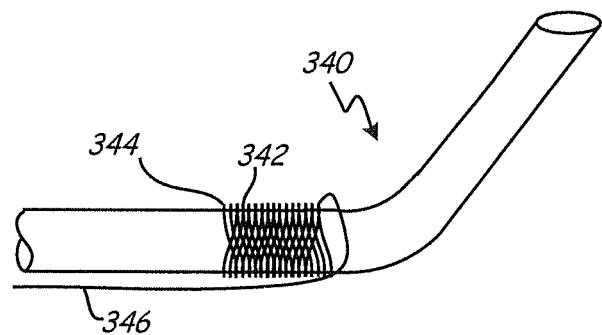
FIG. 18 is a side perspective view of a thrombectomy catheter with a braid structure around the circumference of the catheter for partial occlusion of a vessel.

In alternative or additional embodiments, a flap or other obtrusive feature can be mechanically actuated to increase the overall profile of the catheter. Suitable flaps or the like can be formed, for example, from a soft polymer with shape memory, such as silicone, nylon, PEBAX®, polyurethane, combinations thereof and the like. Alloys, such as stainless steel and/or Nitinol®, can be used to further enhance the shape memory of a polymer. The flap can be restrained against the shaft of the catheter with an external sheath that can be slid longitudinally to deploy the structure, or the structure can be mounted to the shaft to self-expand once the structure exits the guide catheter lumen. An example of such a structure is shown in FIG. 17. Thrombectomy catheter 330 has a flap 332 secured at edge 334 to the catheter body. Pullwire 336 can be used to deploy the flap to a partially occlusive position. The size and position of the flap can be selected to yield a desired partial occlusion of the flow.

In further alternative or additional embodiments, a partial occlusion can be introduced using a braid incorporated into or onto the shaft. A braid can be made from an alloy, such as stainless steel of Nitinol®. The braid can be bare or coated with a soft elastomeric polymer. Compressing the braid longitudinally causes the diameter to increase. A pullwire can be used to induce the compression. An embodiment is shown schematically in FIG. 18. Thrombectomy catheter 340 has a braided structure 342 secured at edge 344 to the catheter body. Pullwire 346 can be used to deploy the braided structure to a partially occluding configuration. As shown in FIGS. 15-18, thrombectomy catheters 300, 316, 326, 340 have a single curve and a suction lumen at the distal end of the catheter, although a similar partially occluding structured can be placed on other thrombectomy structures described herein.

The material selection is significant for the structures described above. The portions of the thrombectomy catheter can be formed from one or more biocompatible materials, including, for example, metals, such as stainless steel or alloys, e.g., Nitinol®, or polymers such as polyether-amide block co-polymer (PEBAX®), nylon (polyamides), polyolefins, polytetrafluoroethylene, polyesters, polyurethanes, polycarbonates, mixtures thereof, copolymers thereof or other suitable biocompatible polymers. Radiopacity can be achieved with the addition of markers, such as platinum-iridium or platinum-tungsten or through radio-pacifiers, such as barium sulfate, bismuth trioxide, bismuth subcarbonate, powdered tungsten, powdered tantalum or the like, added to a polymer.

Generally, different sections of the thrombectomy catheter can be formed from different materials from other sections, and sections of the catheter can comprise a plurality of materials at different locations and/or at a particular location. For example, fittings and the like can be formed form a suitable material, such as one or more metals and/or one or more polymers. In addition, it may be desirable to form a distal section or a portion thereof of the catheter from an elastomeric polymer, such as suitable polyurethanes, polydimethyl siloxane and polytetrafluoroethylene. In addition, selected sections of the catheter can be formed with materials to introduce desired stiffness/flexibility for the particular section of the catheter. For example, it may be desirable to have a flexible portion at or near the distal end of the catheter. In some embodiments, a suitably flexible portion can have a material with a Shore Durometer D value of no more than 50 to achieve desired tracking properties for placement of the catheter.

One material of particular interest is a thermoplastic polymer with embedded metal wire. Suitable polymers include, for example, polyamides, i.e., nylons. The wire can be braided, coiled or otherwise placed over a polymer tubing liner with some tension. A polymer jacket is then placed over the top. Upon heating over the softening temperature of the polymer and subsequent cooling, the wire becomes embedded within the polymer. The liner and jacket can be of the same or different materials. Suitable wire includes, for example, flat stainless steel wire. Some specific examples are described below. The wire adds additional mechanical strength while maintaining appropriate amounts of flexibility.

In general, shaft 106 forming the majority of the length of the catheter is somewhat rigid but flexible enough to bend along the patient's vasculature or other series of vessels. The bending of shaft 106 can cause contact with the vessel wall near branches and/or turns in the vessels, but the flexibility of the tube permits this contact without damaging the vessel. In some embodiments, shaft 106 is formed to have desired resilience with appropriate flexibility by embedding a metal wire within a polymer tube. For example, the metal wire can be a flat ribbon made of stainless steel or Nitinol® with sizes from about 0.0005 inches to about 0.002 inches in thickness and from about 0.001 inches to about 0.005 inches wide. The polymer can be a thermoplastic polymer, such as nylon, PEBAX®, polyurethane, silicone or mixtures thereof. In one embodiment, a coil or braid is threaded onto a polytetrafluoroethylene coated mandrel. A thermoplastic tube is longitudinally split and loaded over the wire on the mandrel. Inert polymer heatshrink tubing can be placed over the thermoplastic. Suitable heat shrink tubing is available in various polymers, such as fluorinated ethylene propylene copolymer (FEP) and polytetrafluoroethylene (PTFE), which are available from Zeus Incorporated, Orangeberg, S.C. The assembly can then be heated past the melt temperature of the thermoplastic until the polymer flows around the coil to create a composite. The heatshrink sleeve and the coated mandrel are then removed.

Figure 19:
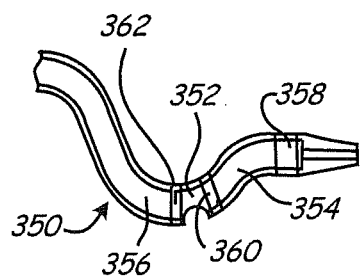
FIG. 19 is a fragmentary side view of a tip portion of a thrombectomy catheter having a stiffer material around a suction port relative to an adjacent more flexible material with several radiopaque markers also shown.

As noted above, the tip portion generally is more flexible than shaft 106. The tip portion generally is resilient enough that the curve of the tip portion is not lost while manipulating the device during delivery. Thermoset polymer materials can be used to form the tip of the catheter. In some embodiments, a material with a Shore D Durometer value of no more than 50 can be used to achieve desired tracking properties for placement of the catheter as well desired contact properties with the vessel wall. In addition, for embodiments with a side port, a small portion of the tip at the side port can be formed from a less flexible material such that the suction function may be less affected from the deformation of the material. An example is shown in FIG. 19. In this fragmentary view of tip portion 350, segment 352 is formed from a material that is stiffer than adjoining segments 354, 356. As shown in FIG. 19, segment 352 is joined at angled interfaces with adjacent segments 354, 356, although in other embodiments straight interfaces around the entire circumference can be used or the stiffer portion may not include the entire circumference of the catheter body. In general, the materials can be joined using thermal bonding techniques, such as conventional thermal bonding techniques. In particular, it may be desirable to form the tip portion or a section thereof from an elastomeric polymer, such as suitable polyurethanes, nylon, PEBAX®, polydimethyl siloxane, polytetrafluoroethylene or mixtures thereof. A portion of the tip generally is made radiopaque. This can be done through the introduction of a suitable material, such as the radiopaque materials discussed above. Radiopaque marker bands 358, 360, 362 are shown in FIG. 19, as an example of suitable placement.

Ancillary Medical Devices

As noted above, the thrombectomy catheter described herein can be used in conjunction with other medical treatment devices, generally devices useful for the treatment of thrombosis and/or removal/collection of emboli. Suitable ancillary devices include, for example, filters, angioplasty balloons, stents, abrasive devices and the like. These devices may or may not be used with the same guide structure as the thrombectomy catheter. When used in conjunction with these additional treatment structures, a treating physician or other health care professional has added flexibility in designing an appropriate treatment for a particular patient.

Filters can be used to collect emboli resulting from thrombus that is dislodged from the thrombectomy procedure but that avoid removal by way of the suction. Commercially available filtration devices include, for example, the RX Accunet™ Embolic Protection System, available from Guidant, Indianapolis, Ind. This Guidant filter is formed from a nickel-titanium alloy in a mesh. Also, Boston Scientific (Boston, Mass.) markets FilterWire EZ™ Embolic Protection System. The Boston Scientific device has a polyurethane filter. See also, U.S. Pat. No. 6,695,813 to Boyle et al., entitled "Embolic Protection Devices," and U.S. Pat. No. 6,391,045 to Kim et al., entitled "Vena Cava Filter," both of which are incorporated herein by reference.

In some embodiments, an embolism protection device can comprise a polymeric substrate (media, sponge), especially an expandable polymer, such as a swelling polymer, a memory polymer or a compressed polymer. Embolism protection devices comprising a swelling polymer, such as hydrogels and/or shape memory fibers, are described further in copending U.S. patent application Ser. No. 10/414,909 to Ogle, entitled "Embolism Protection Devices," incorporated herein by reference. This pending application also describes the delivery of a bioactive agent in conjunction with the embolism protection device. In fiber-based embodiments, the fibers can be organized into a bundle that is deployed within the vessel. Embolism protection devices formed from fibers, such as surface capillary fibers, are described further in copending U.S. patent application Ser. No. 10/795,131 to Ogle et al., entitled "Fiber Based Embolism Protection Device," incorporated herein by reference and Ser. No. 10/979,439 to Galdonik et al., entitled "Steerable Device having A Corewire Within A Tube And A Combination With A Functional Medical Component," incorporated herein by reference.

Suitable angioplasty balloons are described further, for example in U.S. Pat. No. 6,132,824 to Hamlin, entitled "Multilayer Catheter Balloon," incorporated herein by reference. Stent delivery is described further, for example, in U.S. Pat. No. 6,610,069 to Euteneuer et al., entitled "Catheter Support For Stent Delivery," incorporated herein by reference. Various stents and angioplasty balloons are commercially available. Drug coated stents are presently commercially available, such as the pacitaxel eluting Taxus™ stent from Boston Scientific and the sirolimus eluting Cypher™ stent from Johnson & Johnson. Stents and balloons associated with therapeutic agents are described further in U.S. Pat. No. 6,491,617 to Ogle et al., entitled "Medical Articles That Resist Restenosis," incorporated herein by reference. The thrombectomy catheter can be used before and/or after the use of the balloon or delivery of the stent to remove thrombus. Use of the present thrombectomy catheter in combination with stent delivery is described further below.

Various devices have been described that apply forces to a vessel wall to disrupt thrombosis. For example, U.S. Pat. No. 5,053,008 to Bajaj, entitled "Intracardiac Catheter," incorporated herein by reference, describes the use of sonic energy to disrupt plaque. U.S. Pat. No. 5,211,651 to Reger et al., entitled "Catheter Atherotome," incorporated herein by reference, described basket shaped blades that are designed to cut plaque. Similarly, U.S. Pat. No. 5,766,191 to Trerotola, entitled "Percutaneous Mechanical Fragmentation Catheter System," similarly describes a device to cut plaque. The emboli resulting from dislodged thrombus can be collected with a filter. The thrombectomy catheter can be used before and/or after the delivery of mechanical or other disruptive energy to the thrombus in which use before removed thrombus susceptible to suction removal and use after removes thrombus loosened by the previous manipulation.

Method for Using Thrombectomy Catheter

The thrombectomy catheter can be used to remove thrombus from any reasonable vessel within a patient. There are certain common features that are independent of the particular vessel, which are discussed in the following. Common features involve placement of the catheter tip in the vicinity of a legion with thrombus. If appropriate for the particular embodiment of the catheter, the tip can then be converted from a delivery configuration to a curved configuration. Once the catheter tip is at a desired position, suction can be initiated. The guide structure may or may not be removed after positioning the catheter, and the selection of an appropriate procedure may be influenced by the design of the catheter and/or the use of ancillary medical devices. The catheter can be moved to remove thrombus from a swept region. In some embodiments, it is desirable to move the catheter in an upstream direction, which generally corresponds with a distal to proximal direction for common placements of the catheter in most procedures. While it is generally desirable to use the thrombectomy catheter in a less invasive procedure, the vessel can be exposed for entry in a surgical procedure in some embodiments. Three specific applications are described in more detail below to further illustrate features of the methodology.

Figure 20:
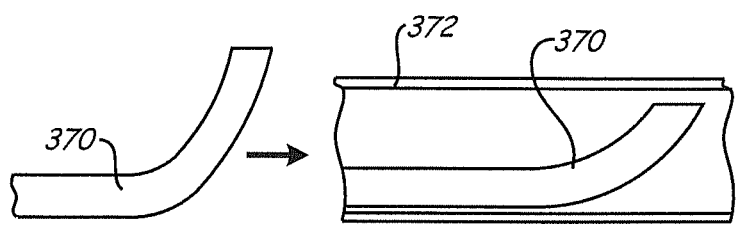
FIG. 20 is a schematic, fragmentary side view of a curved catheter tip portion in an unrestrained view (left side) and a deflected, strained configuration within a vessel (right view).

As noted above, particular thrombectomy catheters are generally intended for use in vessels over a range of sizes. To ensure that the thrombectomy catheters have a suction port adjacent the vessel wall, the deflection distance "D" is generally selected to be larger than the largest vessel diameters selected for use with the particular catheter. Thus, the vessel walls deflect the catheter into a strained configuration with a suction port at or near the vessel wall depending on the location of the suction port in relation to the curves of the tip portion. Such deflection is depicted in FIG. 20. In the left portion of FIG. 20, the un-deflected tip portion 370 is depicted. In the right portion of FIG. 20, tip portion 370 is shown in a strained, deflected configuration within vessel 372.

While the tip portion is shown in FIG. 20 with a suction port at the distal end of the catheter, similar deflection takes place with a side port. Suction ports at the distal end of the catheter may then be essentially in contact with the vessel wall. Side suction ports may or may not be essentially in contact with the vessel wall depending on the positioning of the suction port relative to the curves of the tip portion. The distal tip portion including an unconstrained displacement diameter of at least 90% of a vessel diameter of the patient's vessel, wherein the unconstrained displacement diameter is defined as a perpendicular radial distance from a surface of the distal tip portion to the suction port. In general, the suction port can be within 10 percent of the vessel diameter of the vessel wall, in other embodiments within about 5 percent of the vessel diameter of the vessel and in further embodiments within about 2 percent of the vessel diameter of the vessel wall. A person of ordinary skill in the art will recognize that additional ranges of suction port positioning within the explicit ranges above are contemplated and are within the present disclosure.

Figures 21, 22:
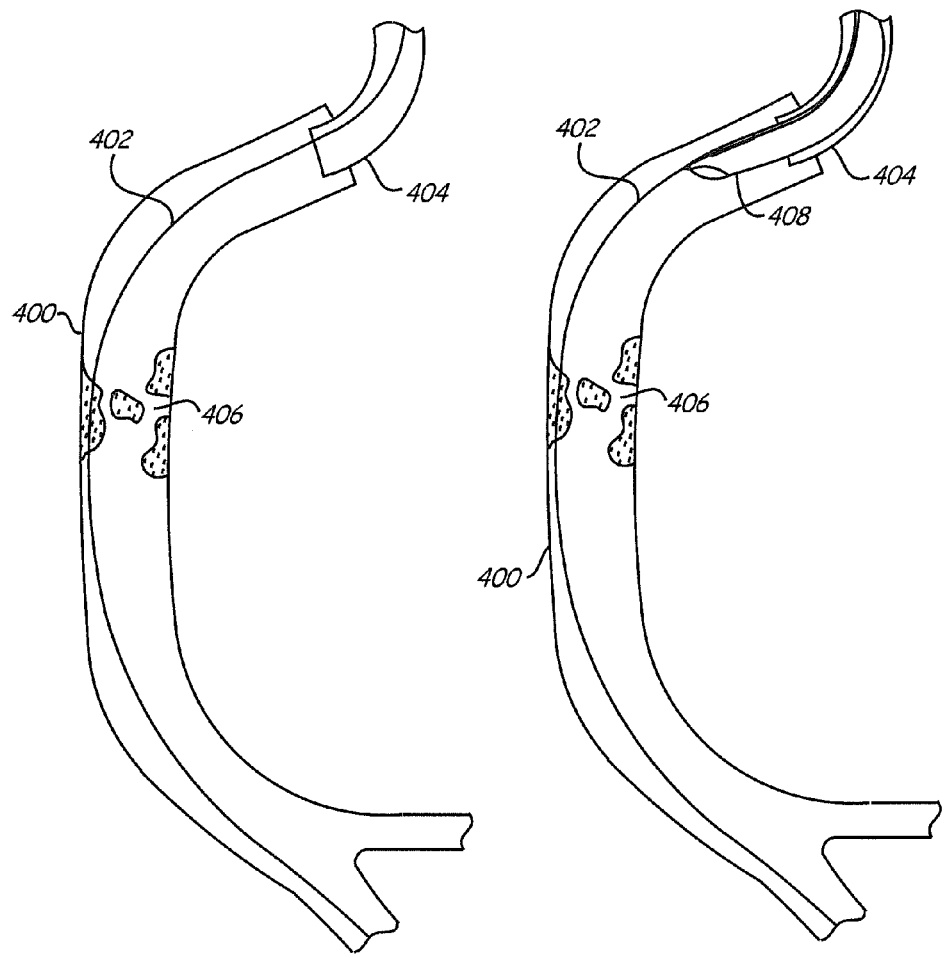
FIG. 21 is a schematic view of a patient's vessel with a guide structure passing by a lesion with thrombus.
FIG. 22 is a schematic side view of the vessel of FIG. 21 with a thrombectomy catheter being positioned within the vessel.
Figure 23:
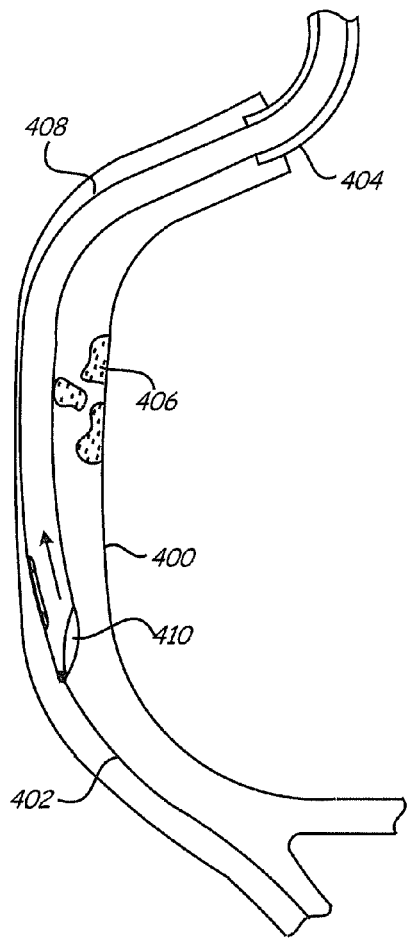
FIG. 23 is a schematic side view of the vessel of FIG. 21 with a thrombectomy catheter in position and its tip being released form a delivery configuration to a curved configuration.
Figure 24:
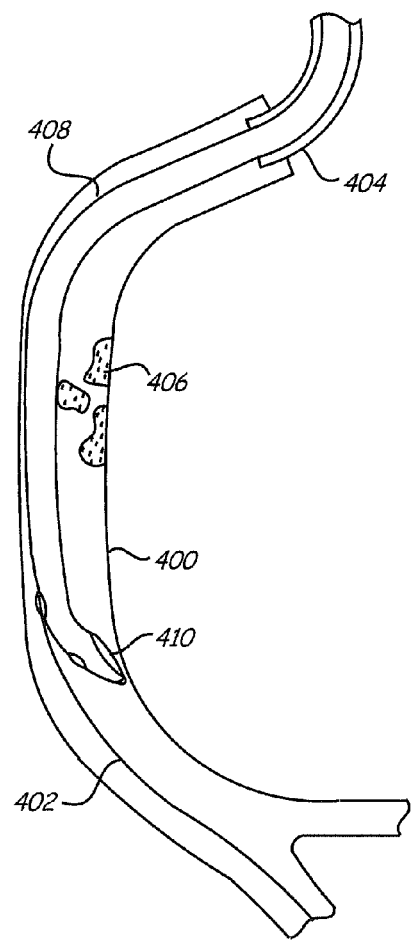
FIG. 24 is a schematic side view of the vessel of FIG. 21 with a thrombectomy catheter of FIG. 23 in a curved configuration.

Referring to FIG. 21, vessel 400 has a guidewire 402 extending from a guide catheter 404. Vessel 400 has a lesion 406 with thrombus/debris. As shown in FIG. 22, thrombectomy catheter 408 can be brought into the vessel along guidewire 402. Referring to FIG. 23, the tip 410 of thrombectomy catheter 408 is inserted past lesion 406. As shown in FIGS. 22-25, thrombectomy catheter 408 has a structure corresponding to the catheter in FIGS. 6-8. Guidewire 404 can be withdrawn to release the tip to its suction configuration, and the guidewire can then be extended outward again as shown in FIG. 24, although alternatively the guidewire can be removed from the patient. Thrombectomy catheters with alternative tip designs can be used similarly, and the tip can be correspondingly positioned in a curved configuration unless the catheter design does not have a delivery configuration.

Figures 25, 26:
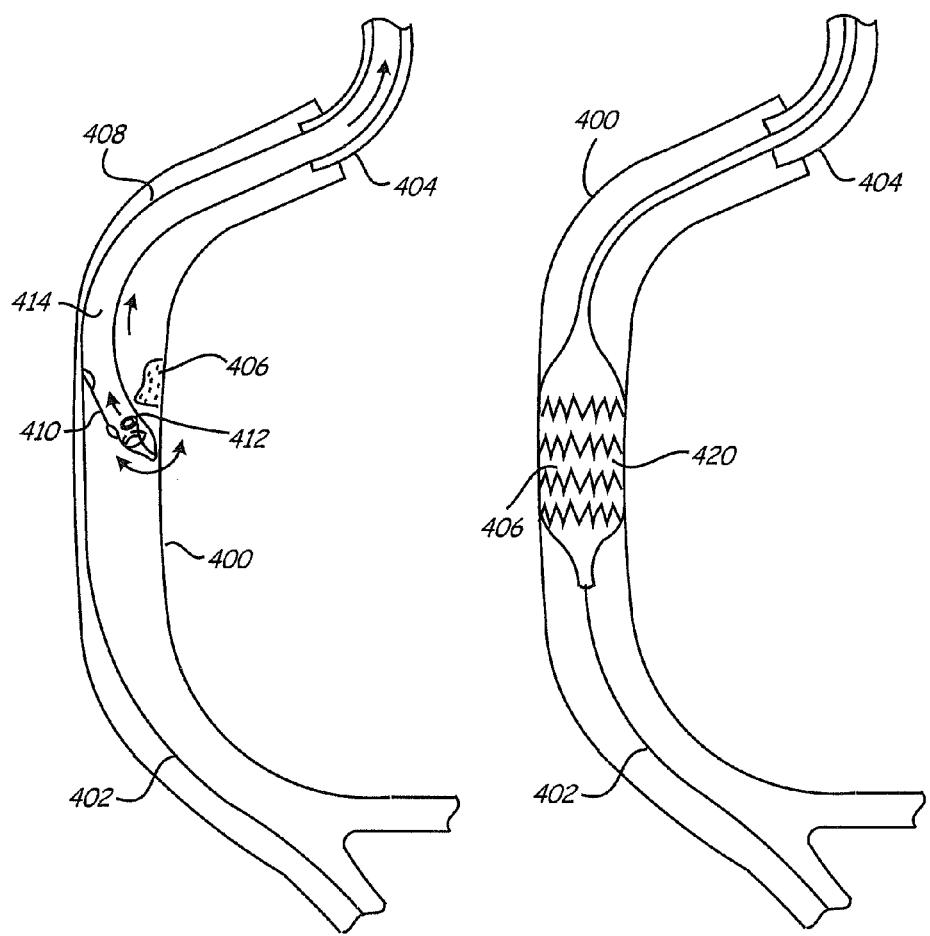
FIG. 25 is a schematic side view of the vessel of FIG. 21 with the thrombectomy catheter of FIG. 24 removing thrombus from the vessel.
FIG. 26 is a schematic side view of the vessel of FIG. 21 with a stent being delivered following removal of the thrombus with a thrombectomy catheter.

Referring to FIG. 25, suction is used to remove thrombus from lesion 406 through catheter 408. Dislodged thrombus (emboli) 412 is depicted within the catheter following removal through the suction lumen 414. The catheter tip 410 can be moved longitudinally along a selected length of vessel 400 as well as circumferentially around the inner circumference of the vessel. Suction can be applied until the desired sections of the vessel interior have been subjected to suction. Referring to FIG. 26, a treatment device 420, such as a stent or angioplasty balloon, is being applied at lesion 406 following completion of the suction process and removal of thrombectomy catheter 408.

In general, suction can be initiated at a selected time to achieve desired objectives for the particular patient. Also, suction can be applied continuously or intermittently. For example, suction can be initiated at a selected time once the catheter tip has cleared the guide catheter. In some embodiments with a delivery configuration, suction can optionally be initiated before transitioning the catheter tip to a curved configuration. For example, with a more extensive lesion, it may be desired to apply some suction with a straighter tip configuration before subsequently curving the tip to a curved configuration.

The suction is contrary to the flow within the vessel. In general, the suction rate can be greater than the flow within the vessel or some fraction of the flow. Specifically, the suction rate can be no more than about 125 percent of the vessel flow, in further embodiments, no more than about 110 percent of the vessel flow, in further embodiments from about 25 percent to about 100 percent and in additional embodiments from about 50 percent to about 80 percent of the unrestricted flow through the vessel. As a particular example, if the unrestricted flow through a coronary artery is 100 milliliters (ml) per minute, the suction rate can be 125 percent of the flow or 125 ml per minute or in further embodiments from about 50 ml to about 90 ml per minute. A person of ordinary skill in the art will recognize that additional ranges of flow rates and flow percentages are contemplated and are within the present disclosure. For syringe based suction embodiments, the size of the syringe can be selected based on the flow in the vessel. Thus, a syringe can be filled in roughly 10 to 30 seconds, for example, for any sized vessel. Multiple syringes can be filled to generate a desired degree of suction.

Various approaches can be used to move the catheter tip along the desired portions of the vessel wall. For example, the catheter tip can be moved longitudinally along a selected path and rotated to a different orientation along the circumference of the vessel wall and then moved longitudinally again. This can be repeated as desired. In some embodiments, the catheter tip is moved circumferentially around the vessel inner wall, then moved longitudinally to position the catheter tip at another transverse position where it is moved circumferentially again, and the process is repeated until the desired section of the vessel has been treated. In some embodiments, the circumferential and longitudinal motions are coupled to combine into a spiral motion. Selected combinations of motion can be use to yield the desired thrombus removal. In some embodiments, it is desirable for the longitudinal motion of the catheter to be in a distal to proximal direction.

Figure 27:
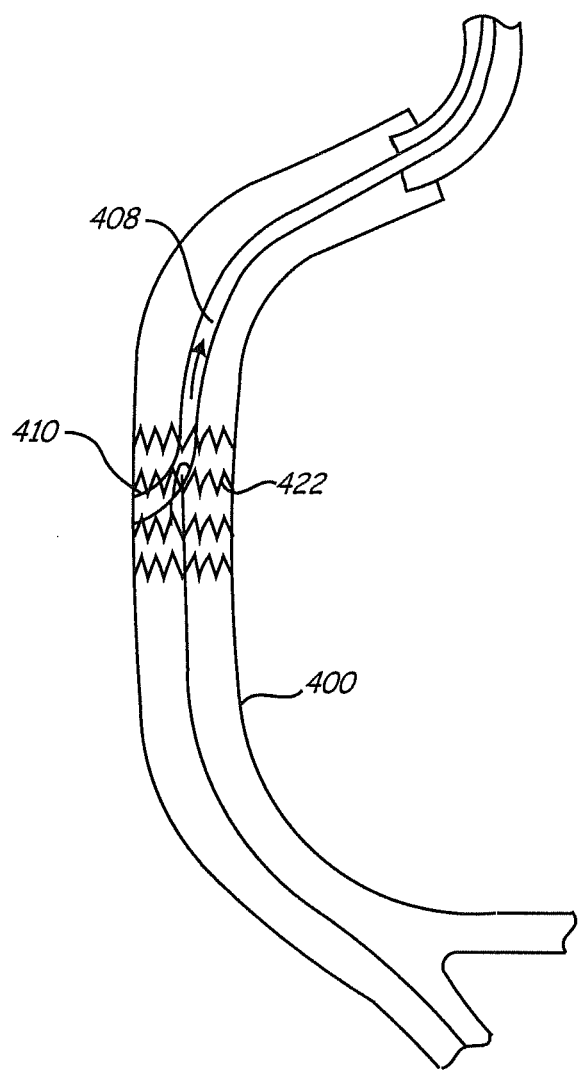
FIG. 27 is a schematic side view of a stent within a vessel and a thrombectomy catheter removing thrombus from within the stent.
Figure 28:
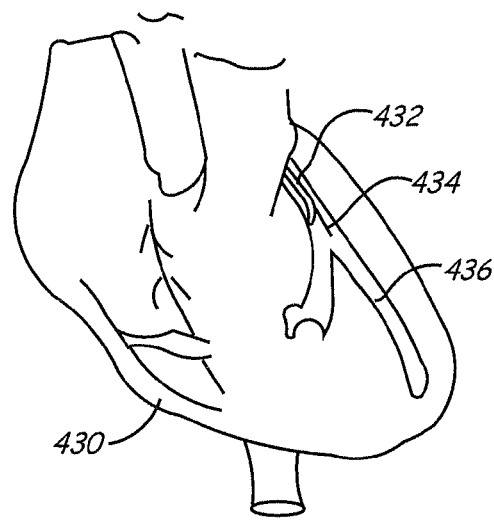
FIG. 28 is a schematic view of a thrombectomy catheter removing thrombus from within a coronary artery.

An alternative or additional embodiment is shown in FIG. 27. In this embodiment, vessel 400 has a stent 422. The stent may or may not have been delivered following thrombectomy based on suction. However, thrombectomy catheter 408 is delivered to position catheter tip 410 within the interior of stent 422. Suction along with suitable movement of the catheter can be used to remove thrombus along the interior of the stent following deployment of the stent. Thus, the thrombectomy catheter can be used to mitigate certain undesired by products of the stent delivery, namely the ultimate formation of emboli.

Figure 29:
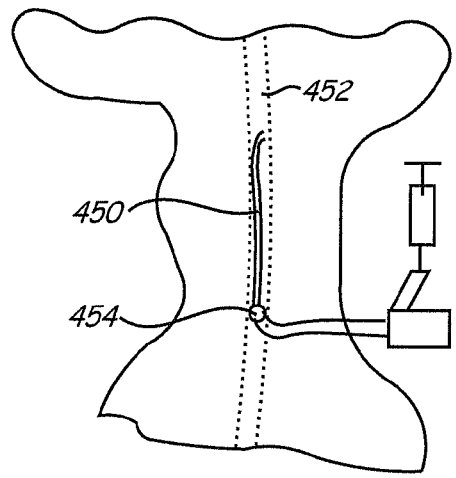
FIG. 29 is a schematic view of a thrombectomy catheter removing thrombus from within a carotid artery.

Referring to FIG. 19, heart 430 is depicted with a thrombectomy catheter 432 on guidewire 434 within coronary artery 436. Thrombectomy catheter 432 can be delivered, for example, using conventional approaches through an incision in the patient's groin or wrist up through arteries to the aorta and into the coronary artery. Referring to FIG. 29, a carotid endarterectomy is depicted using a thrombectomy catheter 450 introduced into a patient's carotid artery 452 through a hemostatic valve 454 at an incision into the patient's neck. In this less invasive procedure, strokes can be mitigated through the removal of thrombus within the carotid artery.

Distribution And Packaging

The medical devices described herein are generally packaged in sterile containers for distribution to medical professionals for use. The articles can be sterilized using various approaches, such as electron beam irradiation, gamma irradiation, ultraviolet irradiation, chemical sterilization, and/or the use of sterile manufacturing and packaging procedures. The articles can be labeled, for example with an appropriate date through which the article is expected to remain in fully functional condition. The components can be packaged individually or together.

Various devices described herein can be packaged together in a kit for convenience. The kit can further include, for example, labeling with instruction for use and/or warnings, such as information specified for inclusion by the Food and Drug administration. Such labeling can be on the outside of the package and/or on separate paper within the package.

The embodiments above are intended to be illustrative and not limiting. Additional embodiments are within the inventive concepts. Although the present invention has been described with reference to particular embodiments, workers skilled in the art will recognize that changes may be made in form and detail without departing from the spirit and scope of the invention.

What is claimed is:

1. A method for the performance of a procedure in a patient's vessel using a catheter having a distal tip portion, a distal end opening, and a suction lumen, wherein the distal end opening is a suction port for providing access to the suction lumen, and wherein the catheter is a rapid exchange catheter comprising a guide port, having a rapid exchange segment between the guide port and the distal end opening, the method comprising:

delivering the catheter on a guide structure into the vessel to a target lesion site wherein the guide structure extends through the guide port and out through the distal end opening to transition the distal tip portion from a natural curved configuration into a relatively straighter configuration;

after the distal tip portion has reached the target lesion site, withdrawing the guide structure sufficiently such that the distal tip portion assumes its natural curved configuration from the relatively straighter configuration, wherein in the natural curved configuration the distal tip portion includes an unconstrained displacement diameter at least 90% of a vessel diameter of the patient's vessel, wherein the unconstrained displacement diameter is defined as a perpendicular radial distance from a surface of the distal tip portion to the suction port; and applying suction with the distal tip portion at the target lesion site to remove debris from the vessel into the suction lumen through the suction port.

2. The method of claim 1 wherein the guide structure comprises a flexible distal section that is sufficiently flexible so that the distal tip portion of the catheter transitions to the natural curved configuration when the guide structure is withdrawn in a proximal direction to appropriately align the flexible distal section with the distal tip portion.

3. The method of claim 2 wherein the guide structure extends through the suction lumen within the rapid exchange segment of the catheter.

4. The method of claim 1 wherein the natural curved configuration of the distal tip portion has a single curve.

5. The method of claim 1 wherein the natural curved configuration of the distal tip portion has a plurality of curves and an additional suction port located along the curves.

6. The method of claim 1 wherein the unconstrained displacement diameter is at least as large as the vessel diameter.

7. The method of claim 1 wherein suction is applied while moving the catheter.

8. The method of claim 1 wherein suction is applied while rotating the catheter.

9. The method of claim 1 wherein the catheter is a single lumen catheter with the guide structure extending through the guide port into the single lumen, wherein the suction lumen extends from a proximal portion of the catheter to the suction port.

10. The method of claim 1 wherein a loading tool is used to facilitate loading of the catheter with the guide structure through the guide port for delivery, the loading tool comprises a rod and a distal cavity that can engage the guide structure, and having dimension suitable for advancement of the rod through the guide port.

11. The method of claim 1 wherein the suction is applied using a syringe connect to the proximal end of the catheter.

12. The method of claim 1 wherein the catheter has an outer diameter from about 0.26 mm to about 3.0 mm.

13. The method of claim 1 wherein the catheter comprises a polymer selected from the group consisting of polyetheramide block co-polymer, nylon (polyamides), polyolefins, polytetrafluoroethylene, polyesters, polyurethanes, polycarbonates, polydimethyl siloxanes, mixtures thereof and copolymers thereof.

14. The method of claim 1 wherein the catheter comprises polymer embedded with metal reinforcement.

15. The method of claim 1 wherein the rapid exchange segment has only one lumen.

16. The method of claim 1 wherein the rapid exchange segment has a reinforcing braid.

17. The method of claim 1 wherein the rapid exchange segment has a radiopaque marker band.

18. The method of claim 1 wherein the guide structure comprises a corewire and an overtube.

* * * * *